(12) United States Patent
Kajino

(10) Patent No.: US 11,417,415 B2
(45) Date of Patent: Aug. 16, 2022

(54) MOLECULAR REPRESENTATION

(71) Applicant: INTERNATIONAL BUSINESS MACHINES CORPORATION, Armonk, NY (US)

(72) Inventor: Hiroshi Kajino, Tokyo (JP)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1042 days.

(21) Appl. No.: 16/100,439

(22) Filed: Aug. 10, 2018

(65) Prior Publication Data

US 2020/0050737 A1 Feb. 13, 2020

(51) Int. Cl.
| | |
|---|---|
| *G06N 5/04* | (2006.01) |
| *G16B 15/00* | (2019.01) |
| *G16B 40/00* | (2019.01) |
| *G06F 40/16* | (2020.01) |
| *G06F 40/154* | (2020.01) |

(52) U.S. Cl.
CPC ........... *G16B 15/00* (2019.02); *G06F 40/154* (2020.01); *G06F 40/16* (2020.01); *G06N 5/046* (2013.01); *G16B 40/00* (2019.02)

(58) Field of Classification Search
CPC .. G06N 3/0454; G06N 3/0427; G06N 3/0472; G06N 5/046; G16B 40/00; G16B 15/00; G16B 40/20; G16C 20/80; G16C 20/70; G06F 40/16; G06F 40/154
See application file for complete search history.

(56) References Cited

U.S. PATENT DOCUMENTS

| | | | | |
|---|---|---|---|---|
| 2011/0295854 | A1* | 12/2011 | Chiticariu | G06F 16/313 707/737 |
| 2012/0054707 | A1* | 3/2012 | Goodman | G06F 30/392 716/119 |
| 2012/0185513 | A1* | 7/2012 | Samukawa | G16C 20/90 707/796 |
| 2012/0284676 | A1* | 11/2012 | Hopkins | G06F 30/392 716/104 |
| 2013/0103632 | A1* | 4/2013 | Ardoint | G06N 5/046 706/47 |
| 2013/0111434 | A1* | 5/2013 | Kajiya | G06F 8/10 717/106 |
| 2014/0096249 | A1* | 4/2014 | Dupont | G06F 21/552 726/23 |
| 2015/0356137 | A1* | 12/2015 | Andros | G06F 16/2246 707/715 |

(Continued)

OTHER PUBLICATIONS

Grace Period Disclosure—Kajino, Hiroshi. "Molecular Hypergraph Grammar," The 32nd Annual Conference of the Japanese Society for Artificial Intelligence, 2018, Jun. 2018, 3E1-04, 4 pages.

(Continued)

*Primary Examiner* — Abdullahi E Salad
(74) *Attorney, Agent, or Firm* — Tutunjian & Bitetto, P.C.; Randall Bluestone

(57) ABSTRACT

Production rules that represent molecule structures are generated by generating a hypergraph from each of a plurality of molecule structures, performing a tree decomposition of each hypergraph to obtain a syntax tree corresponding to the hypergraph, and extracting a set of production rules for producing each hypergraph, by using connections of nodes in the corresponding tree decomposition.

25 Claims, 23 Drawing Sheets

(56) References Cited

U.S. PATENT DOCUMENTS

2016/0173124 A1* 6/2016 Majumdar .......... H03M 7/3097
708/203
2018/0314690 A1* 11/2018 Hwang .................. G06F 40/55

OTHER PUBLICATIONS

Alvin, Christopher Thomas. "Synthesis With Hypergraphs." Louisiana State University Doctoral Dissertations, Aug. 2015, 118 pages.

Pennycuff, Corey et al. "A temporal tree decomposition for generating temporal graphs." arXiv preprint arXiv, Jun. 2017, 1706.09480, 8 pages.

Althaus, Ernst et al. "Graph Rewriting Based Search for Molecular Structures: Definitions, Algorithms, Hardness." Federation of International Conferences on Software Technologies: Applications and Foundations. Jul. 2017, pp. 43-59, Springer, Cham.

Jin, Wengong et al. "Junction Tree Variational Autoencoder for Molecular Graph Generation." arXiv preprint arXiv, Feb. 2018, 1802.04364, 17 pages.

Aguiñaga, Salvador et al. "Growing Graphs from Hyperedge Replacement Graph Grammars." Proceedings of the 25th ACM International on Conference on Information and Knowledge Management. Oct. 2016, pp. 469-478. ACM.

* cited by examiner

FIG. 13
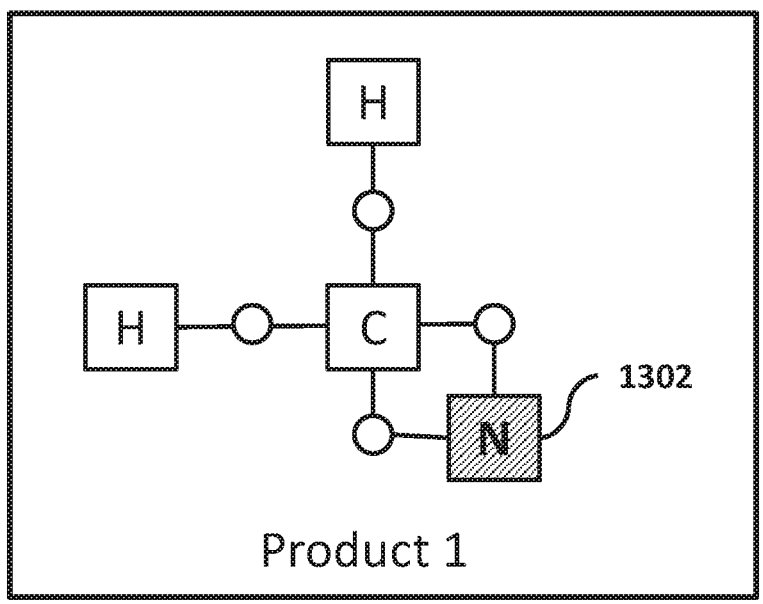
Product 1
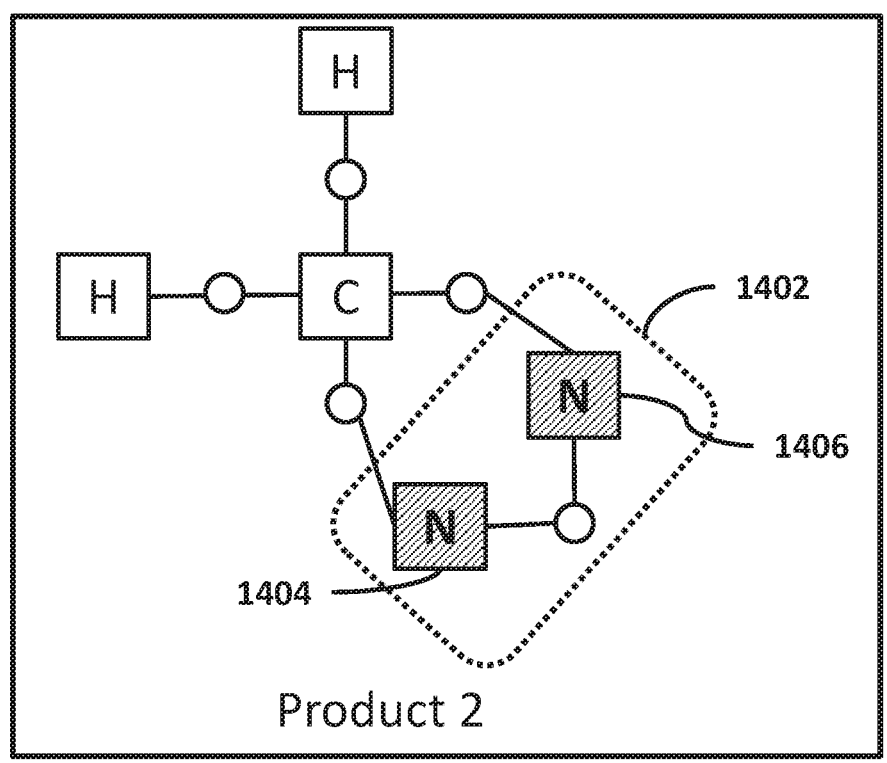
Product 2
FIG. 14

MOLECULAR REPRESENTATION

STATEMENT REGARDING PRIOR DISCLOSURES BY THE INVENTOR OR A JOINT INVENTOR

The following disclosure(s) are submitted under 35 U.S.C. § 102(b)(1)(A):

DISCLOSURE(S): Molecular Hypergraph Grammar, Hiroshi Kajino, May 22, 2018 on the internet (https://confit.atlas.jp/guide/event-img/jsai2018/3E1-04/public/pdf?type=in) and Jun. 7, 2018, 3E1-04, The 32nd Annual Conference of the Japanese Society for Artificial Intelligence, 2018.

BACKGROUND

Technical Field

The present invention relates to a new molecular representation.

Description of the Related Art

Optimal molecular design aims to discover optimal molecules that have desired properties given by a designer. Since molecule structures are too complicated for inputting into a traditional prediction model, latent vectors derived from molecule structures have been used as inputs of the prediction model. Latent vectors are converted from and into Simplified Molecular-Input Line-Entry System (SMILES) strings corresponding to molecule structures using for example variational autoencoders.

However, latent vectors are sometimes converted into invalid SMILES strings (e.g., having invalid valence) due to decoding errors. Thus, traditional prediction models often fail to output valid molecules. In order to output valid molecules, it may be necessary to use complicated neural networks that can learn SMILES' complicated grammar, but this requires a large amount of computational resources.

SUMMARY

According to an aspect of the present invention, a computer-implemented method is provided, including generating a hypergraph from each of a plurality of molecule structures, performing a tree decomposition of each hypergraph to obtain a tree corresponding to the hypergraph, and extracting a set of production rules for producing each hypergraph, by using connections of nodes in the corresponding tree. According to this aspect, latent vectors may be converted into valid molecules by more accurately reflecting valence of atoms.

According to an aspect of the present invention, optionally provided is the method of the preceding aspect, further including removing a redundant hypergraph node in a tree node in the trees before extracting the production rule. According to this aspect, the latent vectors may be converted into valid molecules by excluding invalid connection between atoms.

According to an aspect of the present invention, optionally provided is the method of the preceding aspect, in which the production rules include: one or more starting rules that provide an initial hypergraph portion, and one or more developing rules that connect an additional hypergraph portion to an existing hypergraph portion. According to this aspect, the molecule structures may be efficiently restored from the production rules.

The foregoing aspect may also include an apparatus configured to perform the computer-implemented method, and a computer program product storing instructions embodied on a computer-readable medium or programmable circuitry, that, when executed by a processor or the programmable circuitry, cause the processor or the programmable circuitry to perform the computer-implemented method.

The summary clause does not necessarily describe all features of the embodiments of the present invention. Embodiments of the present invention may also include sub-combinations of the features described above.

BRIEF DESCRIPTION OF THE DRAWINGS

The following description will provide details of preferred embodiments with reference to the following figures wherein:

FIG. 13 shows a hypergraph constructed using the production rules according to an embodiment of the present invention.

FIG. 14 shows a hypergraph constructed using the production rules according to an embodiment of the present invention.

DETAILED DESCRIPTION

Embodiments of the present invention include systems and methods that enable computer systems to more efficiently and more accurately provide prediction models of molecule structures. The improvements to a computer's modelling of molecule structures, realized by embodiments of the present invention, permit computer systems to convert latent vectors into valid molecule structures by more accurately reflecting atom valences without requiring large amounts of computational resources to neural networks using, e.g., the SMILES grammar.

Hereinafter, example embodiments of the present invention will be described. The example embodiments shall not limit the invention according to the claims, and the combinations of the features described in the embodiments are not necessarily essential to the invention.

Figure 1:
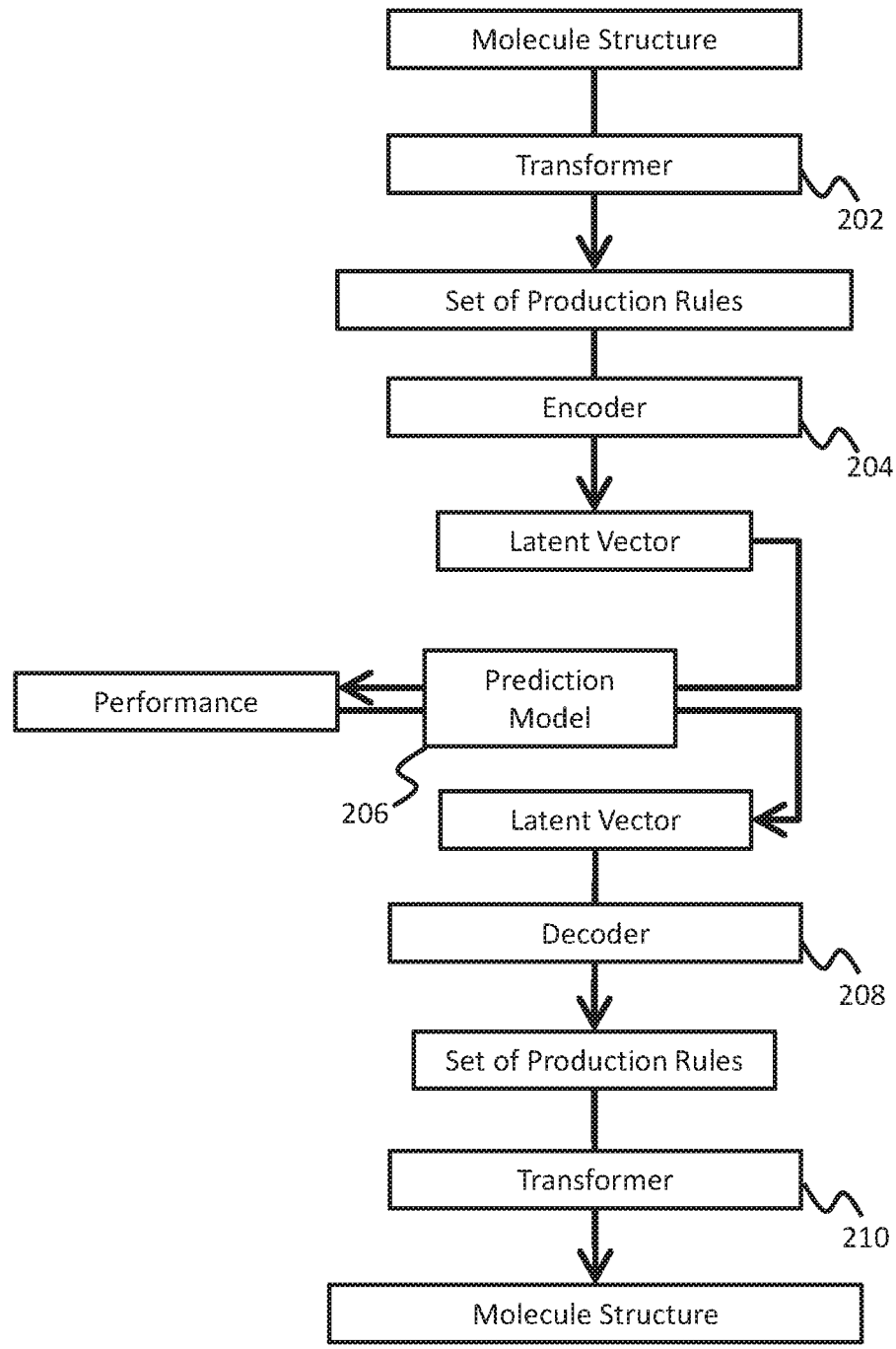
FIG. 1 shows an exemplary framework, according to an embodiment of the present invention.

FIG. 1 shows an exemplary framework, according to an embodiment of the present invention. In the framework, molecule structures are utilized after being transformed into latent vectors, and then converted into the molecule structures from the latent vectors.

A transformer 202 transforms a molecule structure representing a molecule (such as cyclobutane) into a set of production rules. Then, an encoder 204 encodes the set of production rules into a latent vector. The latent vector may be a continuous vector that represents and corresponds to the molecule.

The prediction model 206 predicts a performance of a molecule structure in response to receiving a latent vector corresponding to the molecule structure. In an embodiment, the prediction model 206 may receive a latent vector and output a predicted performance of a molecule corresponding to the latent vector. In an embodiment, the prediction model 206 may be trained with training data including a plurality of sets, each set including a latent vector and a performance.

A latent vector that gives a desired performance is identified by exploring latent vectors using the prediction model 206. The identified latent vector is then decoded into a set of production rules by a decoder 208. The decoded set of production rules is then transformed into a molecule structure that is predicted to provide the desired performance by a transformer 210. The encoder 204 and the decoder 208 may constitute an autoencoder, which can compress dimensions of input data.

In the framework shown in FIG. 1, production rules perform as media between molecule structures and latent vectors. Since the production rules can include chemical constraints, such as valence rules, molecule structures transformed from the production rules are proven to satisfy valence rules, and may be consistent with other chemical constraint, and thus be valid.

Figure 2:
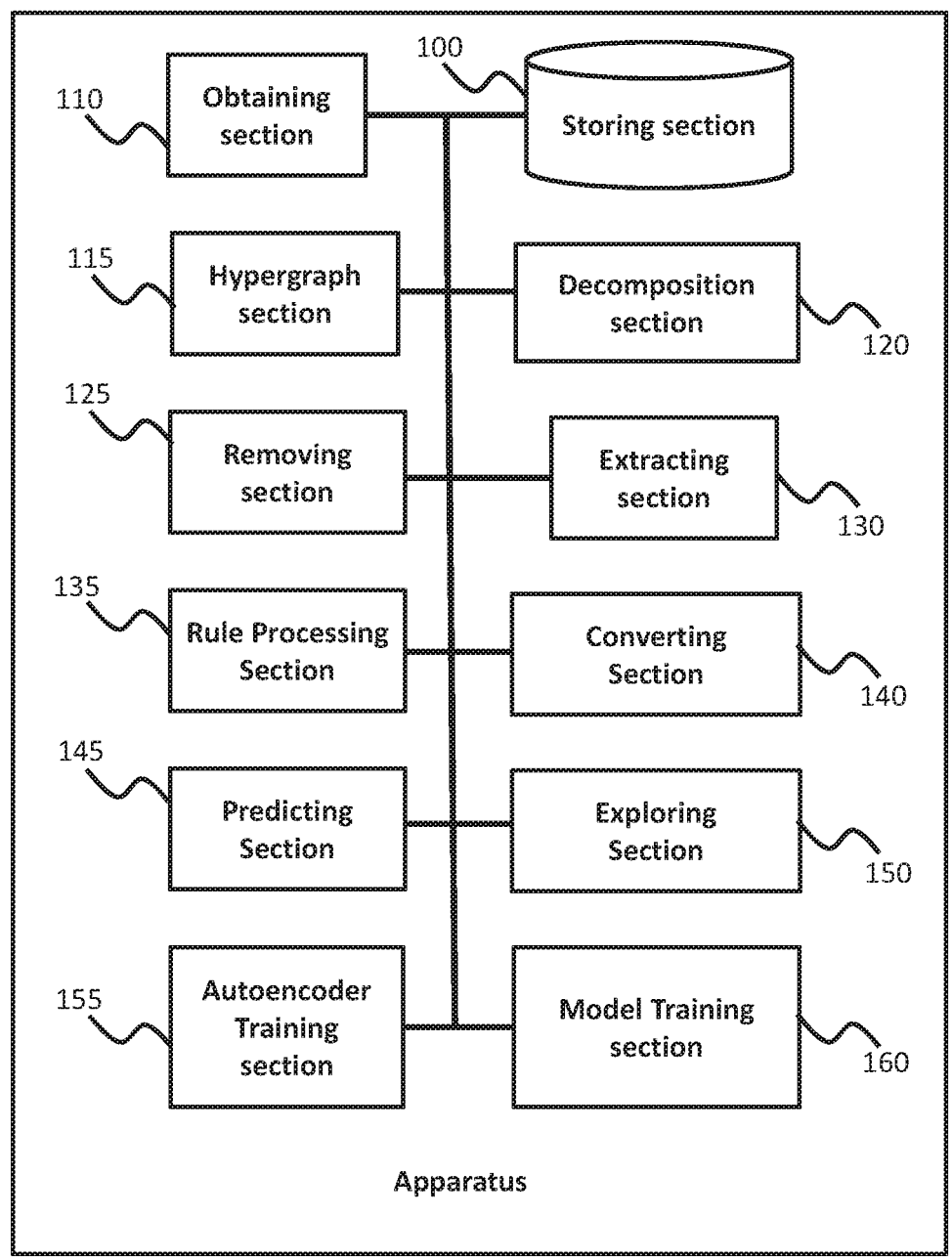
FIG. 2 shows an exemplary configuration of an apparatus, according to an embodiment of the present invention.

FIG. 2 shows an exemplary configuration of an apparatus 10, according to an embodiment of the present invention. The apparatus 10 at least partially implements the framework described in FIG. 1. Thereby, the apparatus 10 restores valid molecule structures by using the production rules instead of SMILES strings.

The apparatus 10 may include a processor and/or programmable circuitry. The apparatus 10 may further include one or more computer readable mediums, for example storing section 100, collectively including instructions. The instructions may be embodied on the computer readable medium and/or the programmable circuitry. The instructions, when executed by the processor or the programmable circuitry, may cause the processor or the programmable circuitry to operate as a plurality of operating sections.

Thereby, the apparatus 10 may be regarded as including a storing section 100, an obtaining section 110, a hypergraph section 115, a decomposition section 120, a removing section 125, an extraction section 130, a rule processing section 135, a converting section 140, a predicting section 145, an exploring section 150, an autoencoder training section 155, and a model training section 160.

In an embodiment, at least a part of the hypergraph section 115, the decomposition section 120, the removing section 125, the extraction section 130, and the rule processing section 135 operates as the transformer 202 and the transformer 210 in FIG. 1. In an embodiment, the converting section 140 may operate as the encoder 204 and the decoder 208 in FIG. 1. In an embodiment, the predicting section 145 may process the prediction model 206 in FIG. 1.

The storing section 100 stores information used for the processing that the apparatus 10 performs. The storing section 100 may also store a variety of data/instructions used for operations of the apparatus 10. One or more other elements in the apparatus 10 (e.g., the obtaining section 110, the hypergraph section 115, the decomposition section 120, the removing section 125, the extraction section 130, the rule processing section 135, the converting section 140, the predicting section 145, the exploring section 150, the autoencoder training section 155, and the model training section 160) may communicate data directly or via the storing section 100, as necessary.

In some embodiments, the apparatus 10 may be implemented by two or more computer devices. For example, the apparatus 10 may be implemented by a device performing as the transformer 202 and the transformer 210, a device performing as the encoder 204 and the decoder 208, and a device processing the prediction model 206.

The storing section 100 may be implemented by a volatile or non-volatile memory of the apparatus 10. In some embodiments, the storing section 100 stores molecule structures, hypergraphs, production rules, an autoencoder, a prediction model, a performance and other data related thereto.

The obtaining section 110 obtains data used for operations of the apparatus 10. For example, the obtaining section 110 may obtain a plurality of molecule structures for extracting production rules, raw training data for training a prediction model, a target molecule structure of which performance is to be predicted, and/or a desired performance for exploring molecules.

The hypergraph section 115 performs an exchange between molecule structures and hypergraphs. In an embodiment, the hypergraph section 115 generates a hypergraph from a molecule structure. The hypergraph section 115 may also generate a molecule structure from a hypergraph.

The decomposition section 120 performs an exchange between the hypergraphs and trees. In an embodiment, the decomposition section 120 performs a tree decomposition of a hypergraph to obtain a tree corresponding to the hypergraph. The decomposition section 120 may also restore a hypergraph from a tree decomposition.

The removing section 125 removes a redundant hypergraph node in a tree node in the tree decompositions before extracting the production rules. The tree decomposition generated by the decomposition section 120 includes a plurality of tree nodes. Each tree node includes one or more hypergraph nodes, a part of which may be redundant. The removing section 125 removes such redundant hypergraph nodes from the tree decompositions. Hereinafter a tree structure of the tree decomposition may be referred to as not only "tree decomposition" but also simply as "tree."

The extracting section 130 extracts a set of production rules for producing a hypergraph, by using connections of nodes in the tree. The extracting section 130 extracts a plurality of sets of production rules from a plurality of trees derived from the plurality of molecule structures. The plurality of sets of production rules may have common production rules. The extracting section 130 extracts a plurality of production rules including rules of a plurality of sets of production rules extracted from a plurality of trees derived from a plurality of molecule structures. The plurality of sets of production rules correspond to the plurality of molecule structures.

The rule processing section 135 processes production rules. In an embodiment, the rule processing section 135 selects one or more production rules among the plurality of production rules that have been extracted from the plurality of trees by the extracting section 120, for producing a hypergraph, from connections of nodes in the tree. Thereby, the rule processing section 135 may convert a tree into a set of production rules including one or more production rules. The rule processing section 135 may also construct a hypergraph from a given set of production rules.

The converting section 140 performs an exchange between the production rules and latent vectors. In an embodiment, the converting section 140 operates as an autoencoder including an encoder and a decoder, for a plurality of sets of production rules. In an embodiment, the converting section converts a set of production rules corresponding to a molecule structure into a latent vector representing the molecule structure as the encoder. The converting section may also restore the set of production rules from the latent vector as the decoder.

The predicting section 145 may predict a performance of a molecule structure. In an embodiment, the predicting section 145 may input the latent vector into a prediction model to obtain a performance of the molecule structure.

The exploring section 150 may explore a latent vector that provides a desired performance in the prediction model.

The autoencoder training section 155 may train the autoencoder performed by the converting section 140. The autoencoder training section 155 may train the autoencoder with a plurality of trees corresponding to a plurality of molecule structures.

The model training section 160 may train the prediction model used by the predicting section 145.

Figure 3:
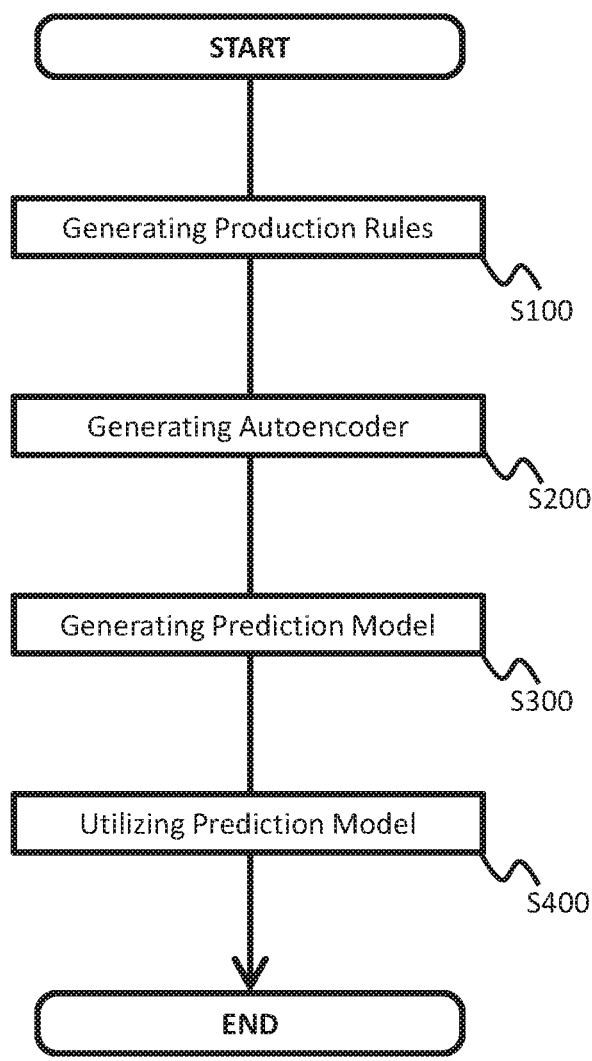
FIG. 3 shows an operational flow according to an embodiment of the present invention.

FIG. 3 shows an operational flow according to an embodiment of the present invention. The present embodiment describes an example in which an apparatus, such as the apparatus 10, performs operations from block S100 to block S400, as shown in FIG. 3.

At block S100, an apparatus, such as the apparatus 10, generates a plurality of production rules from a plurality of molecule structures. Details of block S100 are explained in relation to FIG. 4 below.

At block S200, the apparatus generates an autoencoder to encode a set of production rules into a latent vector by using the plurality of production rules generated at block S100. Details of block S200 are explained in relation to FIG. 20 below.

At block S300, the apparatus generates a prediction model that receives the latent vector and predicts a performance of a molecule structure corresponding to the latent vector using training data. Details of block S300 are explained in relation to FIG. 21 below.

At block S400, the apparatus utilizes the prediction model generated at block S300. In an embodiment, the apparatus may predict a performance of a target molecule structure. In an embodiment, the apparatus may explore a molecule structure that has a target performance. Details of block S400 are explained in relation to FIGS. 22-23 below.

Figure 4:
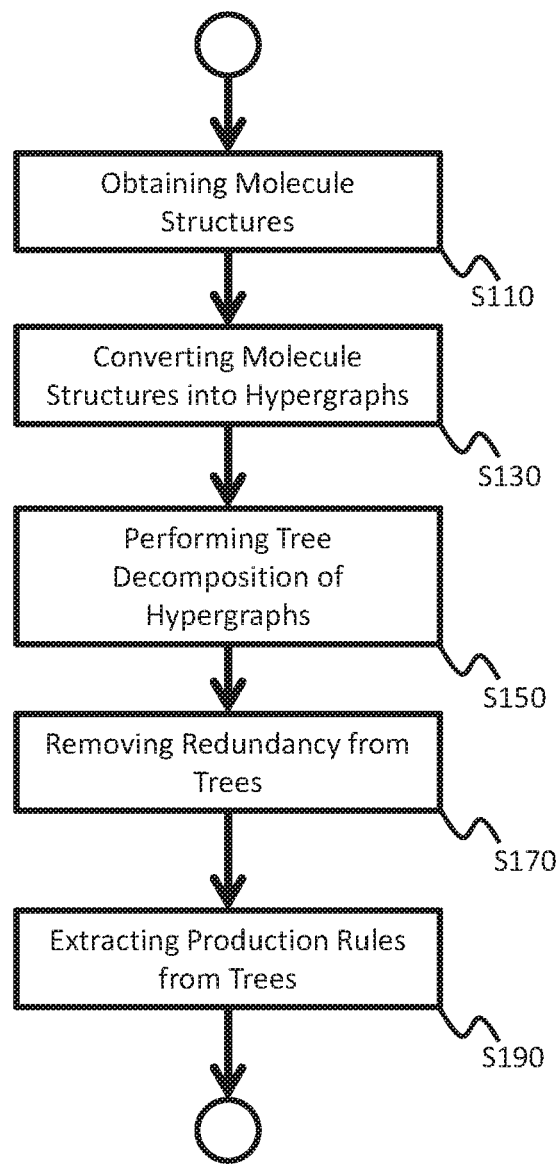
FIG. 4 shows a sub-flow of the flow in FIG. 3 according to an embodiment of the present invention.

FIG. 4 shows a sub-flow of block S100 in the flow of FIG. 3 according to an embodiment of the present invention. The apparatus performs operations of blocks S110-S190 of FIG. 4 at block S100 of FIG. 3.

At block S110, an obtaining section, such as the obtaining section block S110, obtains a plurality of molecule structures of molecules. Each molecule structure may be a simplified representation of a molecule. The molecule structure may include atoms in the molecule and connections between the atoms. In an embodiment, the molecule structure may be a molecular graph of the molecule.

Figure 5:
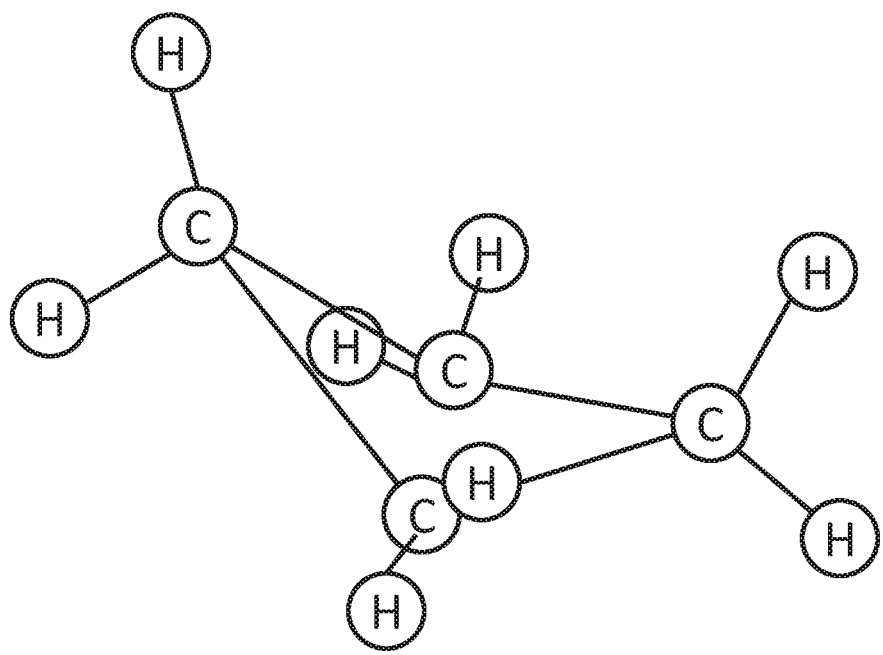
FIG. 5 shows an exemplary 3D conformation of cyclobutane.
Figure 6:
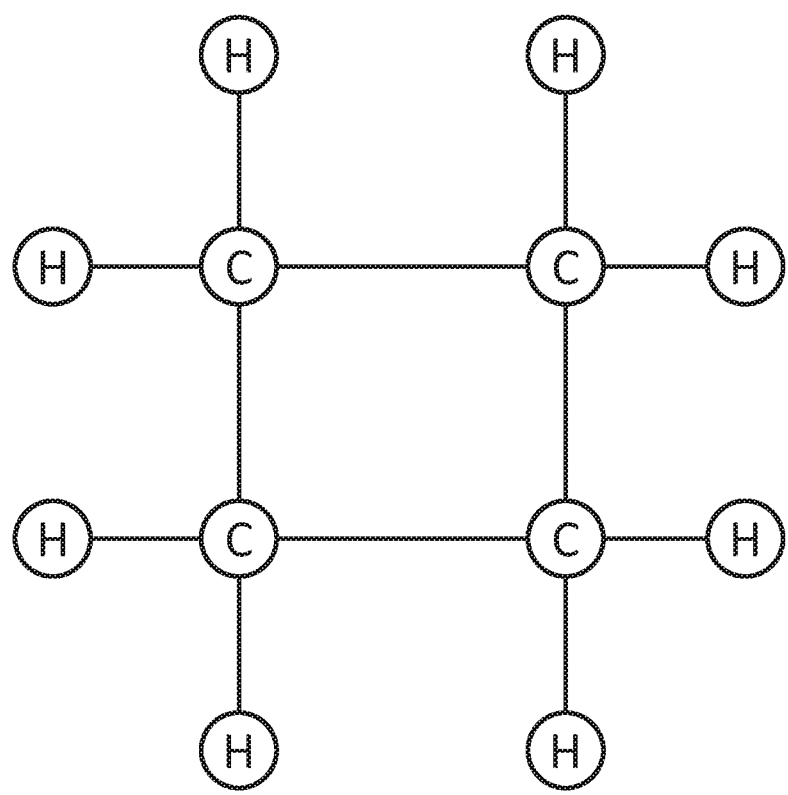
FIG. 6 shows a molecular graph of cyclobutane.

FIG. 5 shows an exemplary 3D conformation of cyclobutane. FIG. 6 shows a molecular graph of cyclobutane. For example, the obtaining section may obtain a molecule graph described in FIG. 6 as a molecule structure of a molecule of cyclobutane described in FIG. 5. In FIG. 6, "C" represents a node representing a carbon atom, "H" represents a node representing a hydrogen atom, and edges between the nodes represents connections between atoms.

At block S130, a hypergraph section, such as the hypergraph section 115 (FIG. 2), converts the plurality of molecule structures obtained at block S110 into a plurality of hypergraphs. In an embodiment, the hypergraph section may generate a hypergraph from each of a plurality of molecule structures.

In an embodiment, each hypergraph of the plurality of hypergraphs may include one or more hyperedges and one or more nodes. The one or more hyperedges may each correspond to an atom in the corresponding molecule structure. The one or more nodes may each correspond to a connection between atoms in the molecule structures. In an embodiment, a hyperedge may correspond to a group of atoms. For example, carbon atoms and hydrogen atoms in benzene may be collectively represented as "B" in a hypergraph.

The hypergraph section may perform the conversion by any known algorithm. In an embodiment, the hypergraph section replaces nodes and edges in molecule structures with hyperedges and nodes of hypergraphs.

Figure 7:
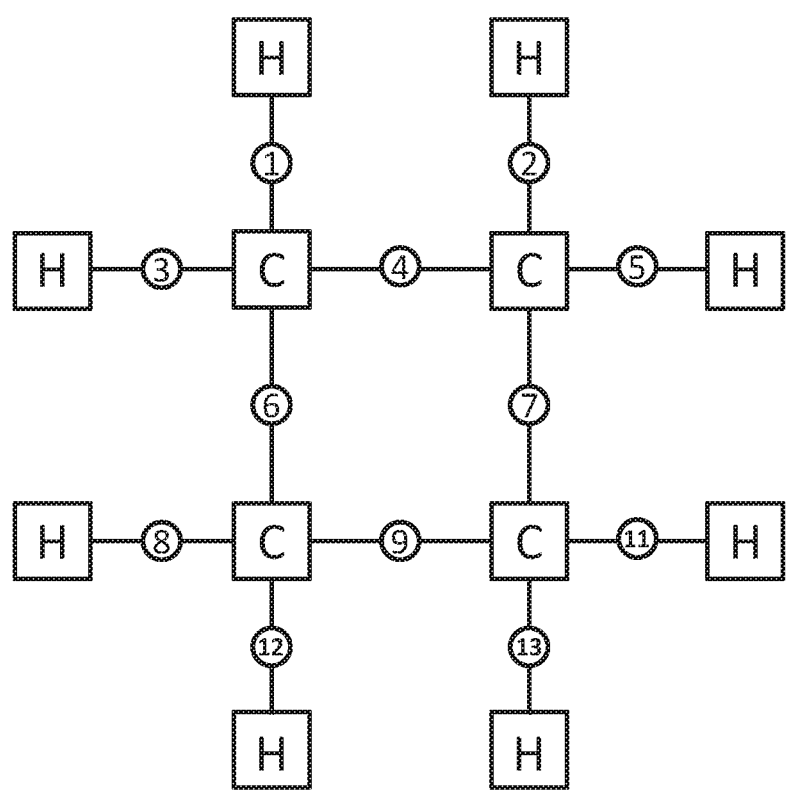
FIG. 7 shows a hypergraph of cyclobutane according to an embodiment of the present invention.

FIG. 7 shows a hypergraph of cyclobutane according to an embodiment of the present invention. The hypergraph section generates the hypergraph described in FIG. 7 from the molecular graph described in FIG. 6. In FIG. 7, "C" and "H" are hyperedges and the small circles having numbers 1-13 are nodes in hypergraph structure. The connection between a hyperedge and a node indicates that the node is a member of the hyperedge.

The hypergraph in FIG. 7 includes one type of nodes representing a single bond. In other embodiments, the hypergraph may include two or more types of nodes. For example, the hypergraph may include a first node representing a single bond, a second node representing a double bond, and a third node representing a triple bond. In another embodiment, multiple bonds are represented by multiple single bonds. For example, a hyperedge "C" and another hyperedge "C" may be connected via two parallel nodes in a hypergraph to represent a double bond.

At block S150, a decomposition section, such as the decomposition section 120 (FIG. 2), performs a tree decomposition of each hypergraph of the plurality of hypergraphs to obtain a tree corresponding to the hypergraph. Thereby, the decomposition section may transform the plurality of hypergraphs having a hypergraph structure obtained at block S130, into a plurality of trees having a tree structure. The tree may include one or more tree nodes, each of which includes a partial structure of a corresponding hypergraph. In an embodiment, the decomposition section may perform the tree decomposition by utilizing a known algorithm such as Maximum Cardinality Search.

Figure 8:
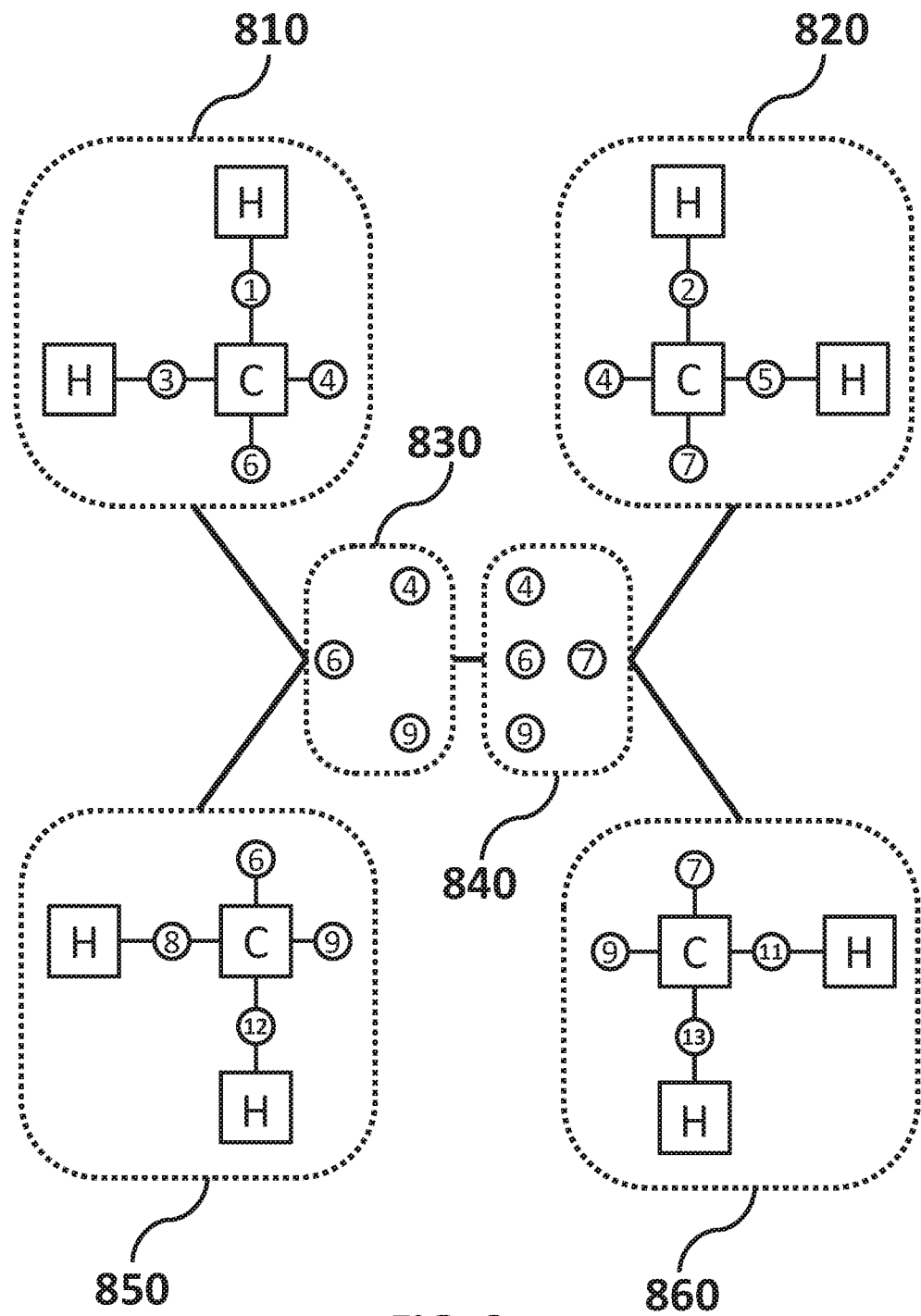
FIG. 8 shows a tree decomposition corresponding to cyclobutane according to an embodiment of the present invention.

FIG. 8 shows a tree decomposition corresponding to cyclobutane according to an embodiment of the present invention. The decomposition section may generate the tree described in FIG. 8 from the hypergraph described in FIG. 7. In FIG. 8, the tree has a tree node 810, a tree node 820, a tree node 830, a tree node 840, a tree node 850, and a tree node 860. The tree nodes 810-860 each include a partial structure of the hypergraph described in FIG. 7.

For example, the tree node 810 includes one "C" and two "H" and 1st, 3rd, 4th, and 6th nodes in the hypergraph. The tree node 820 includes one "C" and two "H" and 2nd, 4th, 5th, and 7th nodes in the hypergraph. The tree node 830 includes 4th, 6th, and 9th node in the hypergraph, and the tree node 840 includes 2nd, 4th, 6th, and 9th nodes in the hypergraph.

In a tree made by the tree decomposition, a tree node may sometimes include a redundant node. For example, in the tree node 840, a 6th node is regarded as redundant; if the 6th node were removed from the tree node 840, the tree nodes including the 6th node would be connected, thus satisfying the definition of tree decomposition At block S170, a removing section, such as the removing section 125 (FIG. 2), removes a redundant hypergraph node in a tree node in the trees. Thereby, the removing section 125 may remove a redundancy from the plurality of trees to obtain a plurality of trees.

Figure 9:
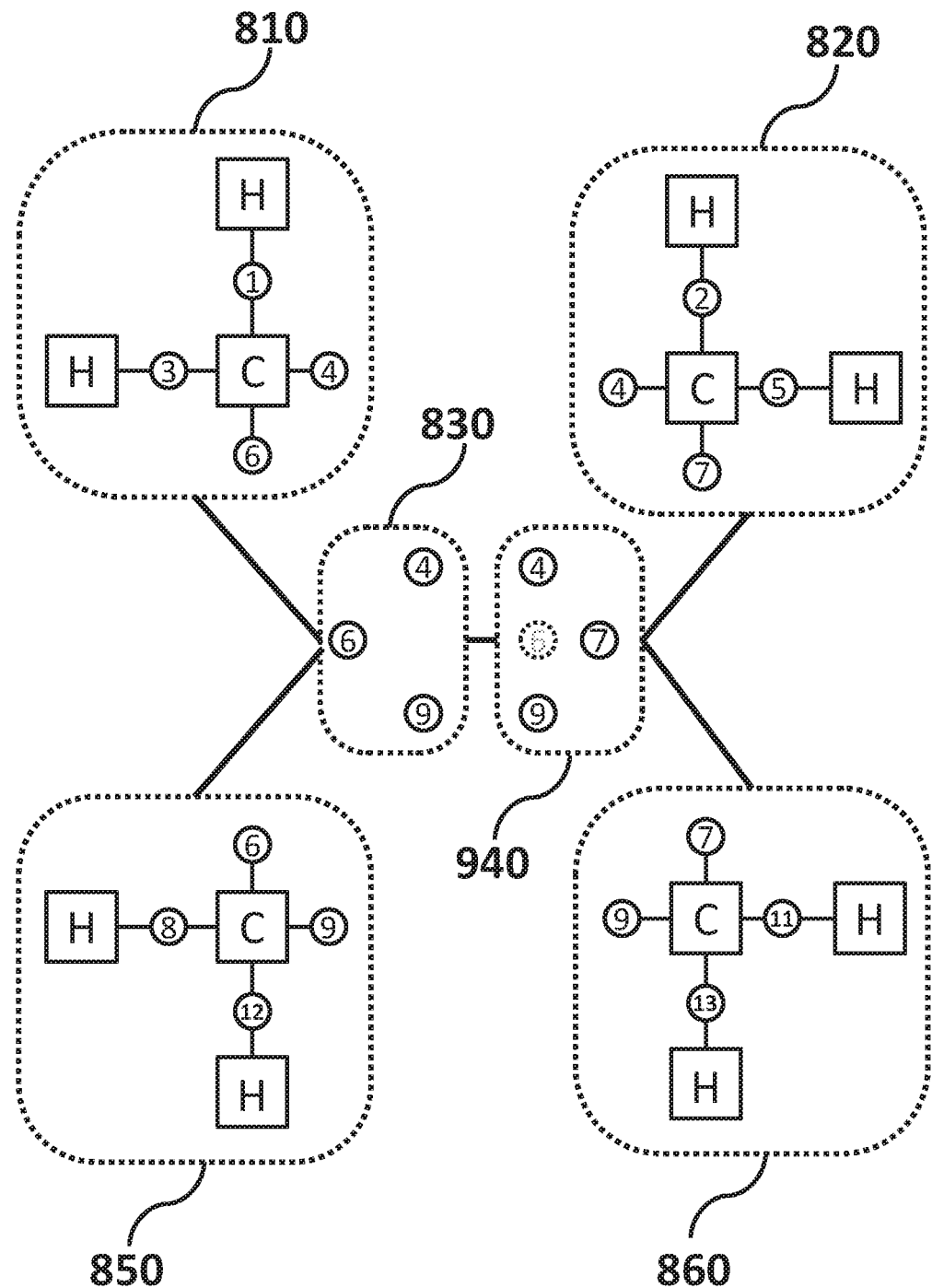
FIG. 9 shows a tree decomposition corresponding to cyclobutane without redundancy according to an embodiment of the present invention.

FIG. 9 shows a tree decomposition corresponding to cyclobutane without redundancy according to an embodiment of the present invention. The removing section generates the tree described in FIG. 9 from the tree described in FIG. 8 by removing the 6th node in the tree node 940, which corresponds to the tree node 840 in FIG. 8.

At block S190, an extracting section, such as the extracting section 130 (FIG. 2), may extract a set of production rules for producing each molecular hypergraph of the plurality of molecules. In an embodiment, the extracting section may extract the set of production rules from each tree among the plurality of trees from which redundancy has been removed by the removing section at block S170. In another embodiment, the extracting section may use the plurality of trees generated at block S150.

The extracting section may extract a set of production rules such that a sequence of the production rules in the set can construct a hypergraph corresponding to the tree with each production rule. In an embodiment, the extraction section may extract a set of production rules by using connections of nodes in the corresponding tree.

In an embodiment, each set of production rules may include information of an order of the production rules in the set. The set of production rules may be represented by a syntax tree induced by the production rules represented as a rooted ordered tree, or a sequence of production rules. For example, each node of a syntax tree corresponds to each of the set of production rules, especially, the root node corresponds to the starting rule, and ordered edges of a syntax tree between a parent node and its children indicate which production rule replaces which non-terminal hyperedge in the parent node's production rule.

In an embodiment, the set of production rules may be represented by a sequence derived from the syntax tree. In the embodiment, the sequence may be determined by searching nodes in the syntax tree with a predetermined method (e.g., depth-first search or breadth-first search). As such, in the embodiment the sequence may be a depth-first traversal or breadth-first traversal of the syntax tree.

In an embodiment, the extracting section utilizes a known algorithm to infer a hyperedge replacement grammar (or HRG) for extracting the production rules. HRG provides a set of construction rules for constructing a hypergraph from a syntax tree. For example, the extracting section may utilize an algorithm based on hyperedge replacement graph grammars.

In a specific example, the extracting section may infer HRG using definition 1, stating: a hyperedge replacement grammar is a tuple $G=(N, T, S, P)$, where N is a set of non-terminal hyperedge labels, T is a set of terminal hyperedge labels, $S \in N$ is a starting non-terminal hyperedge, and P is a set of production rules. Production rule $P=(A, R)$, where $A \in N$ is a non-terminal symbol, R is a hypergraph with hyperedge labels $T \cup N$ and has $|A|$ external nodes.

The extracting section may extract a plurality of sets of production rules from the plurality of trees. Production rules among the plurality of sets of production rules may constitute a plurality of production rules. In an embodiment, the extracting section may extract a set of production rules so as not to increase new production rules by utilizing as many already extracted rules as possible.

In an embodiment, the extracting section may extract two or more different sets of production rules for each hypergraph. For example, the decomposition section may generate two or more of trees from one hypergraph, and the extracting section may extract the two or more different sets from the two or more of trees. Thereby, each molecule structure may be evaluated from different aspects.

In an embodiment, the production rules may include one or more starting rules, and, one or more developing rules. In an embodiment, the starting rules may provide an initial hypergraph portion. The initial hypergraph portion may include (A) one or more hyperedges including at least one of (a1) one or more non-terminal symbols and (a2) one or more terminal symbols, and, (B) one or more nodes.

The (a2) one or more terminal symbols and (B) one or more nodes may constitute a hypergraph or a partial structure of the hypergraph. Thereby, the initial hypergraph portion includes the partial structure of the hypergraph. The one or more non-terminal symbols may connect to the partial structure of the hypergraph.

The developing rules may replace a non-terminal symbol in an existing hypergraph portion with an additional hypergraph portion. In an embodiment, the additional hypergraph portion includes (A) one or more hyperedges including at least one of (i) one or more non-terminal symbols and (ii) one or more terminal symbols, and, (B) one or more nodes.

In an embodiment, each non-terminal symbol represents a portion to be replaced with the additional hypergraph portion by the developing rule. In an embodiment, each terminal symbol represents an atom in the molecule structures.

Figure 10:
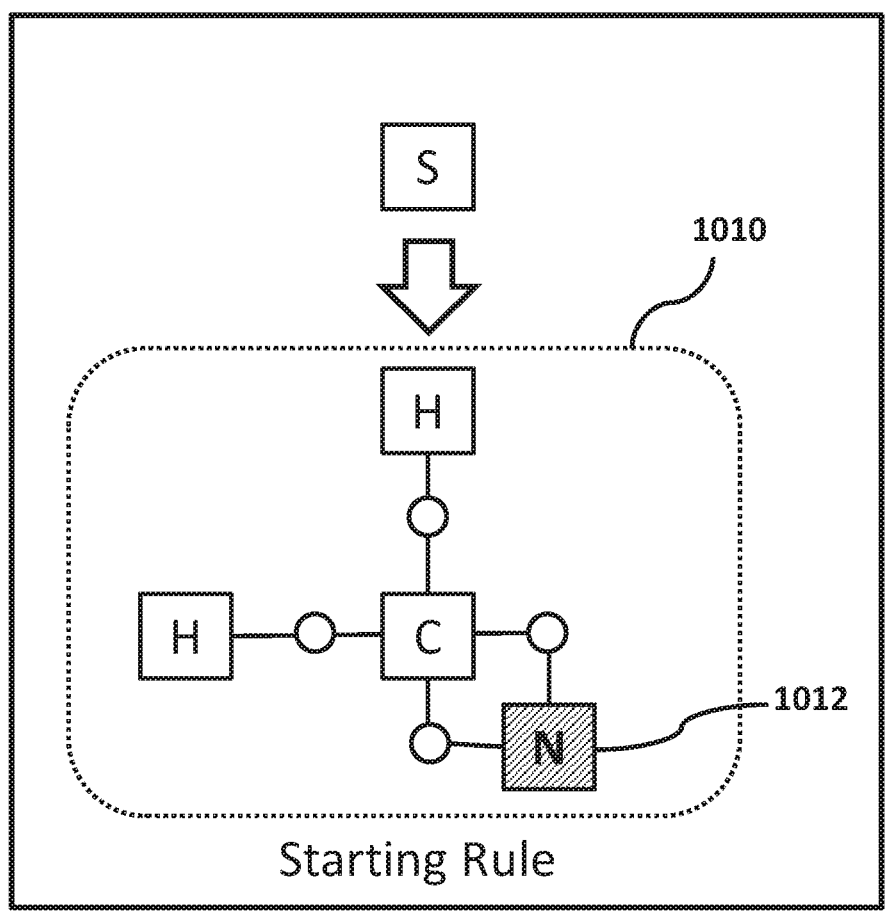
FIG. 10 shows a production rule according to an embodiment of the present invention.
Figure 11:
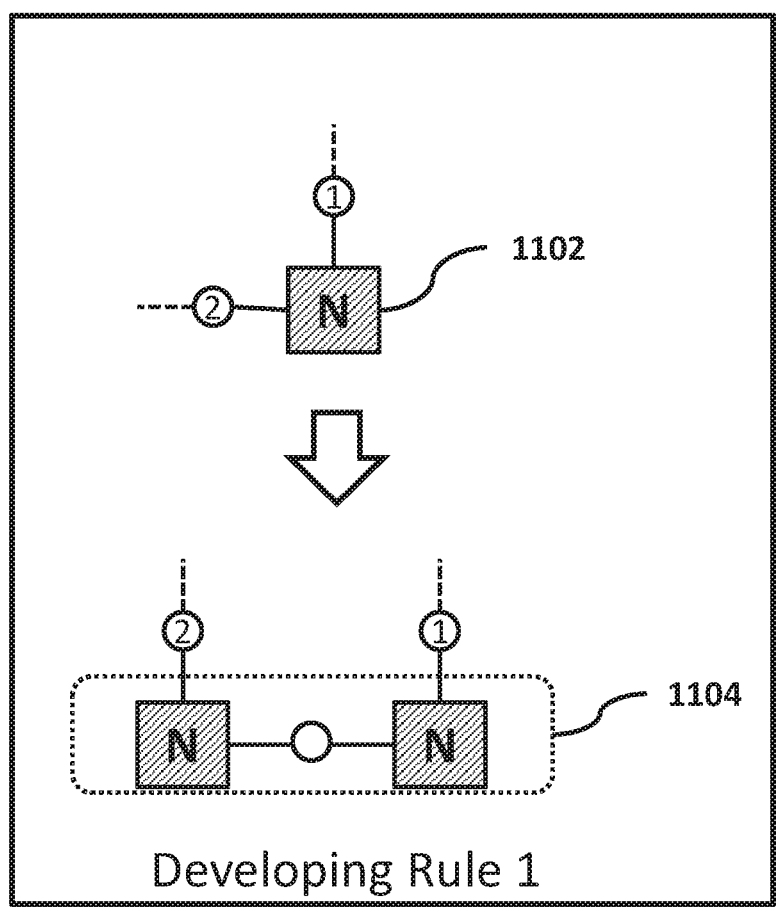
FIG. 11 shows a production rule according to an embodiment of the present invention.
Figure 12:
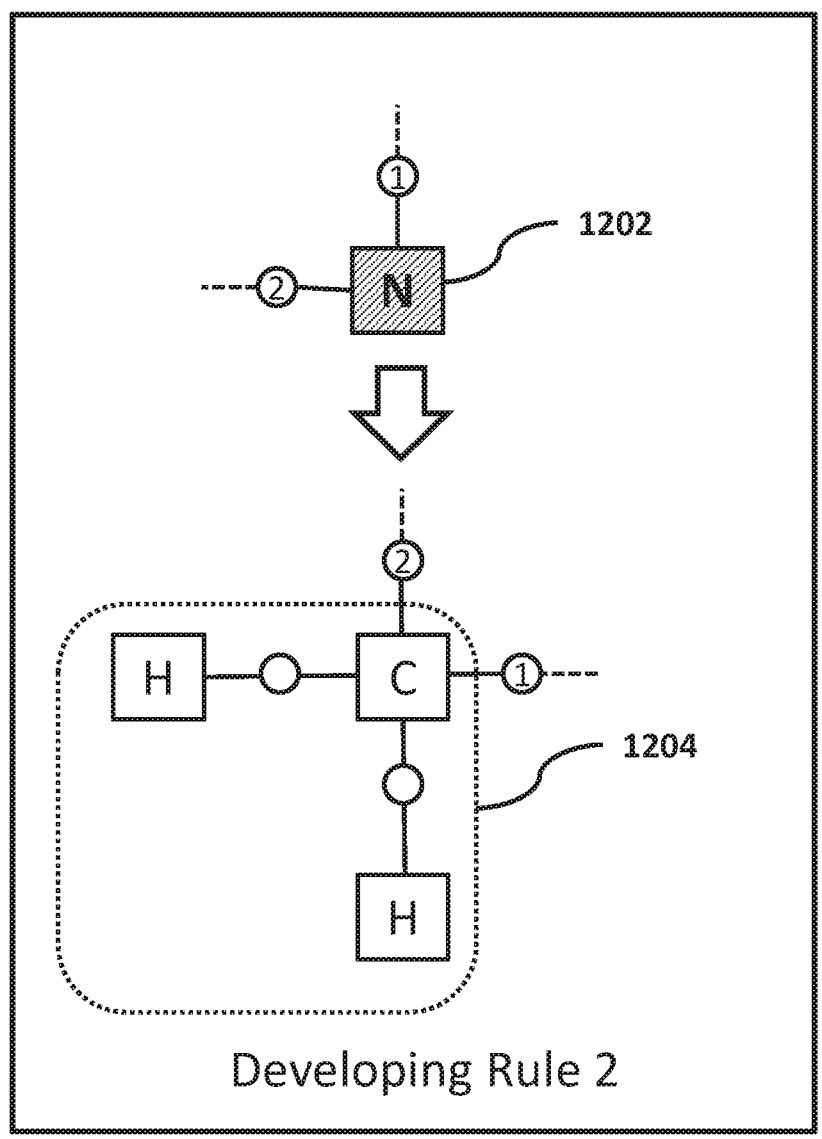
FIG. 12 shows a production rule according to an embodiment of the present invention.

FIGS. 10-12 show production rules according to an embodiment of the present invention.

FIG. 10 shows a starting rule. The starting rule replaces an initial symbol shown as "S" with an initial hypergraph portion 1010. The initial hypergraph portion 1010 has a structure corresponding to a hypergraph portion 810 in FIG. 9 and a non-terminal symbol 1012 shown as "N". The non-terminal symbol 1012 connects to the nodes connecting "C". In the initial hypergraph portion 1010, "C" and "H" are terminal symbols.

FIG. 11 shows a developing rule 1. The developing rule 1 replaces the non-terminal symbol 1102 shown as "N" with an additional hypergraph portion 1104. The additional hypergraph portion 1104 includes two non-terminal symbols shown as "N" and a node between them.

FIG. 12 shows a developing rule 2. The developing rule 2 replaces the non-terminal symbol 1202 shown as "N" with an additional hypergraph portion 1204. The additional hypergraph portion 1204 includes three terminal symbols shown as "C" and "H" and two nodes between them.

In an embodiment, the extracting section may extract the starting rule and the developing rules 1-2 described in FIGS. 10-12 as a set of production rules, from the tree described in FIG. 9 at block S190. A combination of the starting rule and the developing rules 1-2 enables construction of the hypergraph described in FIG. 7 that corresponds to the tree in FIG. 9.

FIGS. 13-18 show how to construct a hypergraph by using the production rules according to an embodiment of the present invention.

FIG. 13 shows that the starting rule provides an initial hypergraph portion 1302 (reference numeral 1010 of FIG. 10) shown as product 1. FIG. 14 shows that the non-terminal symbol 1302 in product 1 (FIG. 13) is replaced with the additional hypergraph portion 1402 by the developing rule 1 in FIG. 11 to provide product 2.

Figure 15:
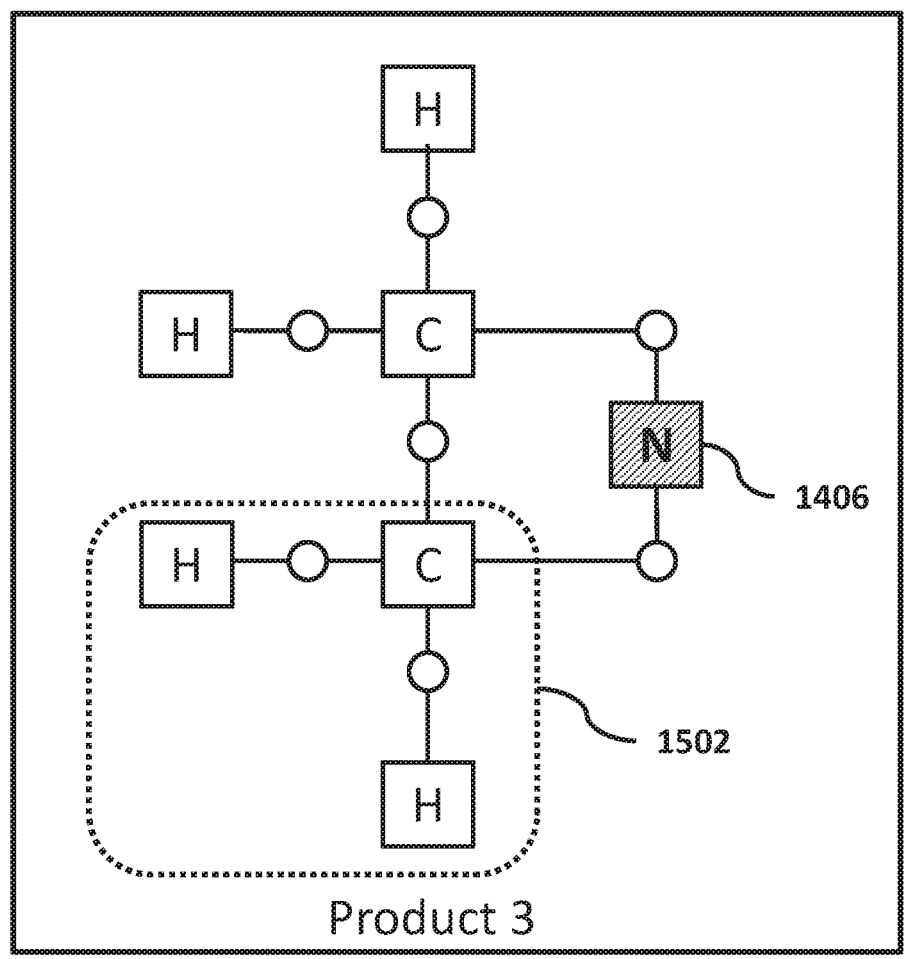
FIG. 15 shows a hypergraph constructed using the production rules according to an embodiment of the present invention.

FIG. 15 shows that the non-terminal symbol 1404 in product 2 (FIG. 14) is replaced with the additional hypergraph portion 1502 by the developing rule 2 in FIG. 12 to provide product 3. The non-terminal symbol 1406 is maintained.

Figure 16:
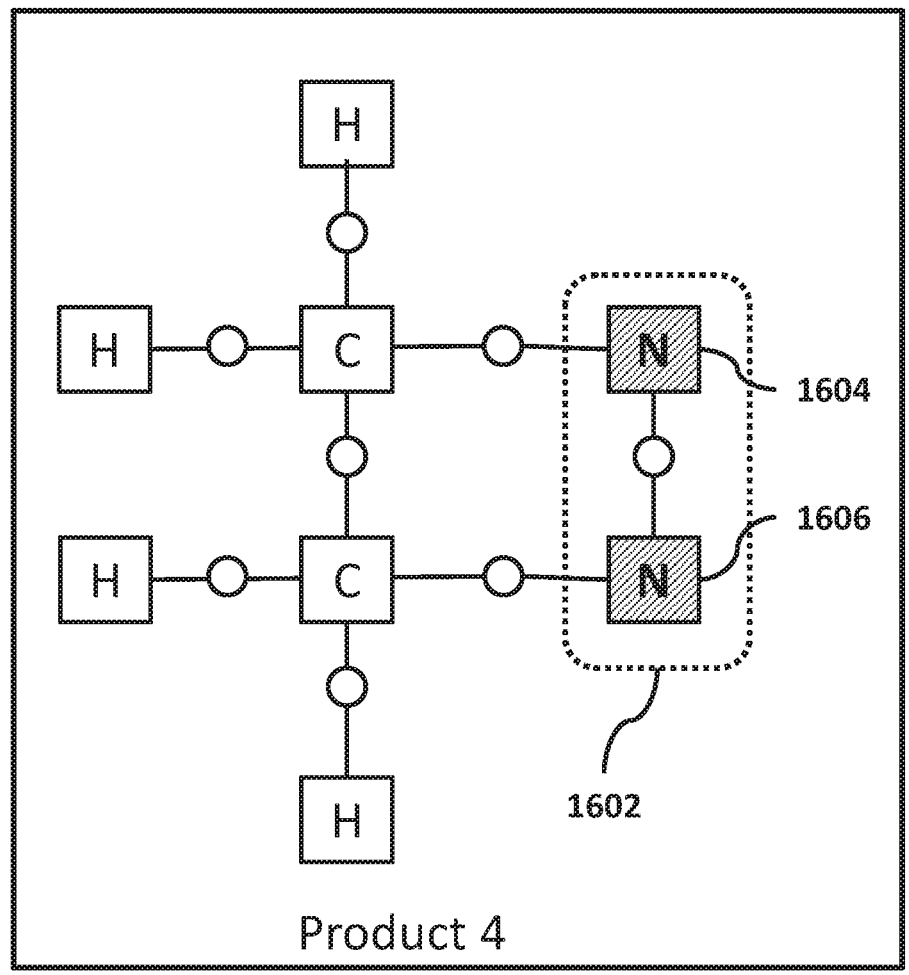
FIG. 16 shows a hypergraph constructed using the production rules according to an embodiment of the present invention.

FIG. 16 shows that the non-terminal symbol 1406 in product 3 (FIG. 15) is replaced with the additional hypergraph portion 1602, having non-terminal symbols 1604 and 1606, by the developing rule 1 in FIG. 11 to provide product 4.

Figure 17:
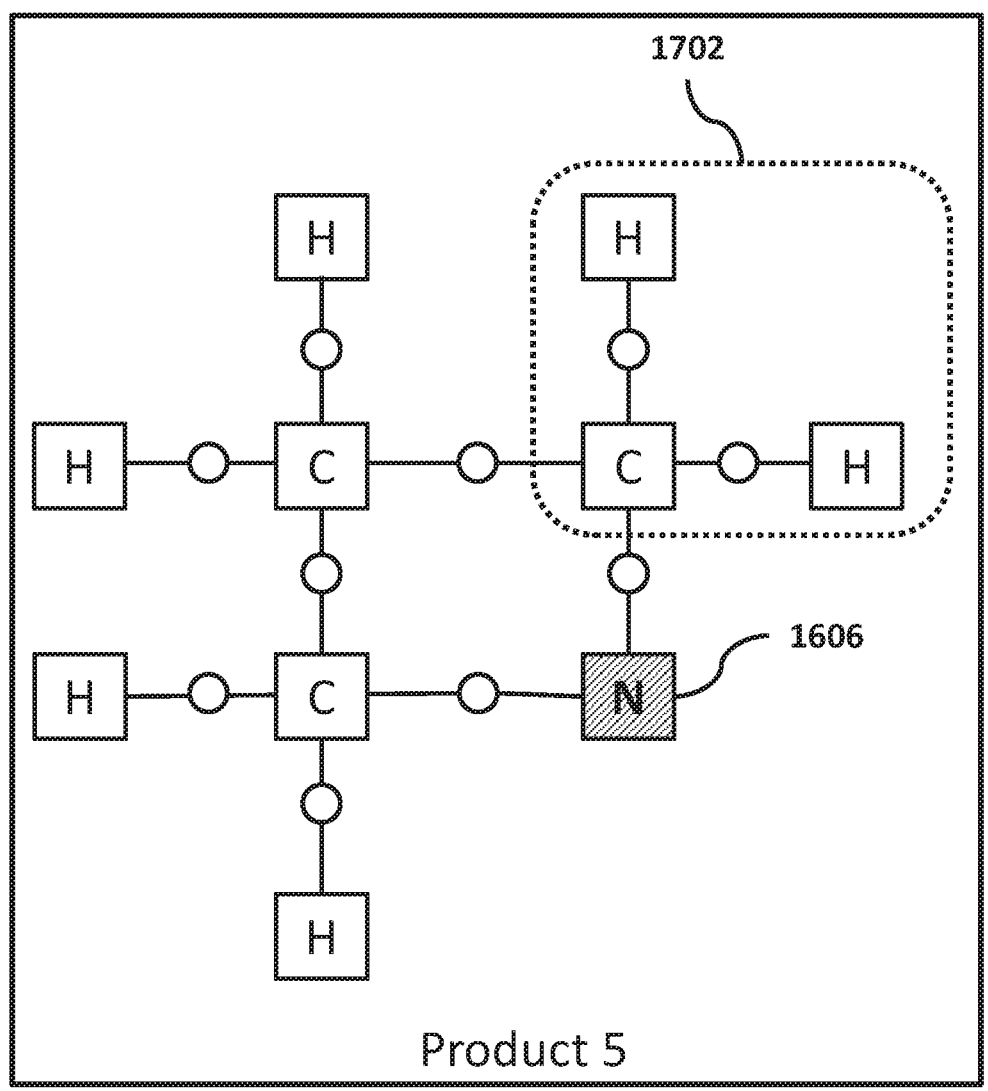
FIG. 17 shows a hypergraph constructed using the production rules according to an embodiment of the present invention.

FIG. 17 shows that the non-terminal symbol 1604 in product 4 (FIG. 16) is replaced with the additional hypergraph portion 1702 by the developing rule 2 in FIG. 12 to provide product 5. The non-terminal symbol 1606 is maintained.

Figure 18:
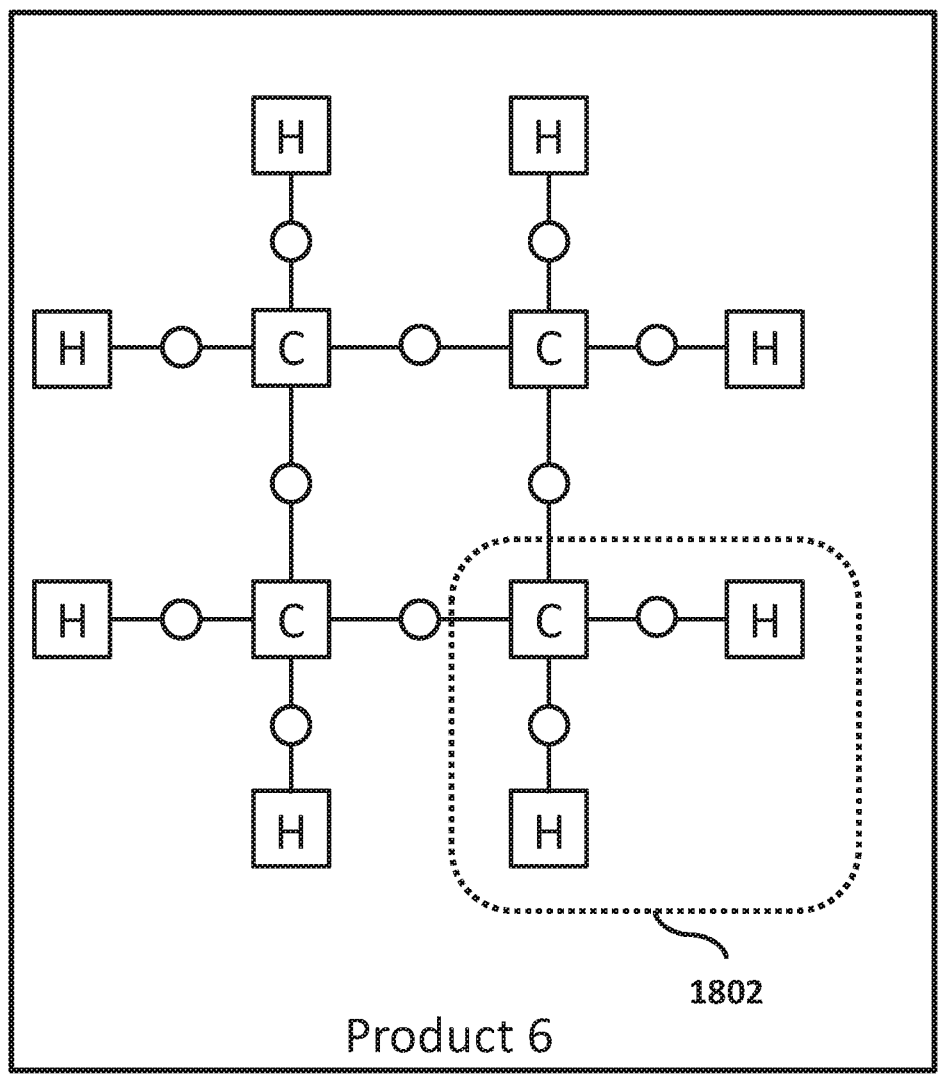
FIG. 18 shows a hypergraph constructed using the production rules according to an embodiment of the present invention.

FIG. 18 shows that the non-terminal symbol 1606 in product 5 (FIG. 17) is replaced with the additional hypergraph portion 1802 by the developing rule 2 in FIG. 12 to provide product 6. The hypergraph shown in FIG. 18 is substantially the same as the hypergraph shown in FIG. 7.

As explained in relation to FIGS. 10-18, the extracting section may extract production rules to restore a hypergraph from a tree decomposed from the hypergraph. The extraction section may extract a large number of production rules from a large number of trees derived from a variety of molecule structures. Thereby, a variety of molecule structures, at least molecule structures obtained at block S110, can be restored by the transformer 210 in FIG. 1.

Figure 19:
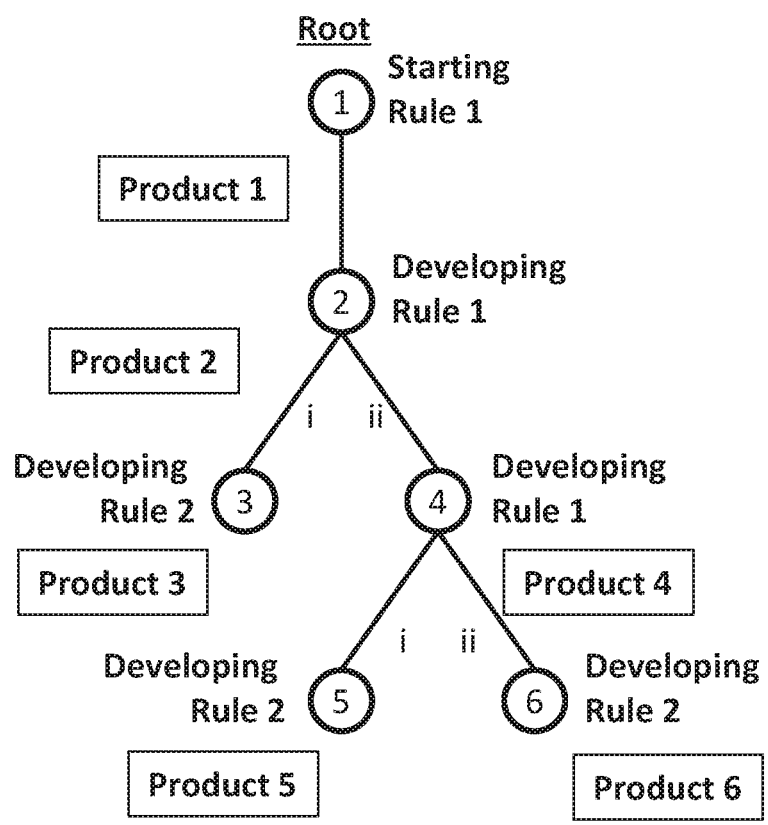
FIG. 19 shows a syntax tree corresponding to a set of production rules for cyclobutane.

FIG. 19 shows a syntax tree corresponding to a set of production rules for cyclobutane. The syntax tree in FIG. 19 is an ordered tree including 6 nodes, one of which is a root node. Each node in the syntax tree corresponds to each production rule. For example, a root node (shown as "1") corresponds to the starting rule, and the other nodes (shown as "2" ... "6") corresponding to developing rules 1-2.

The syntax tree may include one or more pairs of a parent node and one or more child nodes. For example, a node "1" is a parent node and a node "2" is a child node within them, and a node "2" is a parent node and nodes "3" and "4" are child nodes within them. Within a parent-child relationship, the parent node may include M non-terminal symbols, the non-terminal symbols in the parent node may be ordered (1 ... M), and edges between the parent node and child nodes may be ordered (such as shown as "i" and "ii" in FIG. 19).

When applying the breadth-first search to the syntax tree, starting rule (shown in FIG. 10) is first applied at the node "1" to produce product 1 (shown in FIG. 13). Then developing rule 1 (shown in FIG. 11) is applied at the node "2" to produce product 2 (shown in FIG. 14). Then developing rule 2 (shown in FIG. 12) is applied at the node "3" to produce product 3 (shown in FIG. 15), and then developing rule 1 (shown in FIG. 11) is applied at the node "4" to produce product 4 (shown in FIG. 16). Then developing rule 2 (shown in FIG. 12) is applied at the node "5" to produce product 5 (shown in FIG. 17), and then finally developing rule 2 (shown in FIG. 12) is applied at the node "6" to produce product 6 (shown in FIG. 18).

In this specific example, a set of production rules for cyclobutane may be a sequence (1, 2, 3, 2, 3, 3) that is a sequence of starting rule (representing "1"), developing rule 1 (representing "2"), developing rule 2 (representing "3"), developing rule 1, developing rule 2 and developing rule 2, which can be derived from the syntax tree of FIG. 19.

Figure 20:
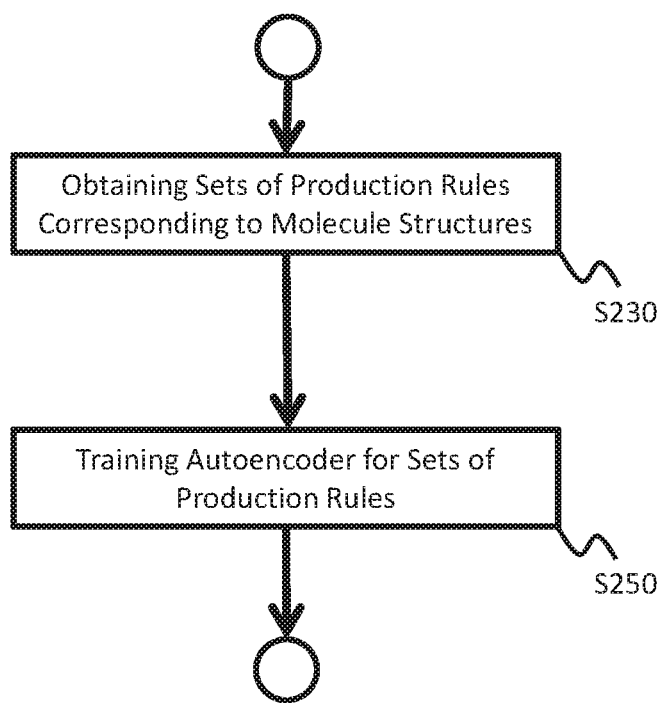
FIG. 20 shows a sub-flow of the flow in FIG. 3 according to an embodiment of the present invention.

FIG. 20 shows a sub-flow of block S200 in the flow of FIG. 3 according to an embodiment of the present invention. The apparatus may perform operations of block S230 and block S250 of FIG. 20 at the operation of block S200 of FIG. 3.

At block S230, an autoencoder training section, such as the autoencoder training section 155 (FIG. 2), may obtain a plurality of sets of production rules. In an embodiment, the autoencoder training section obtains at least a part of the plurality of sets of production rules that the extracting section has extracted at block S190 in FIG. 4. Here each set of the plurality of production rules may correspond to a molecule structure among a plurality of molecule structures.

At block S250, the autoencoder training section may train an autoencoder for the plurality of sets of production rules. In an embodiment, the autoencoder training section trains a neural network that includes both of (A) an encoder that inputs each set of production rules and outputs a latent vector, and (B) a decoder that inputs the latent layer output from the encoder and restores the set of production rules that the encoder inputs.

In an embodiment, an encoder includes one or more layers in a neural network and a decoder includes one or more layers that are located downstream from the encoder in the neural network. The autoencoder training section may perform the training by a known method. In an embodiment, the autoencoder may be a conventional autoencoder or a variational autoencoder.

In another embodiment, the autoencoder training section automatically generates a plurality of sets of production rules and uses the plurality of sets for the training of the autoencoder. In such embodiment, the autoencoder training section excludes invalid sets of production rules that provide invalid molecules or that violates the inferred HRG.

Figure 21:
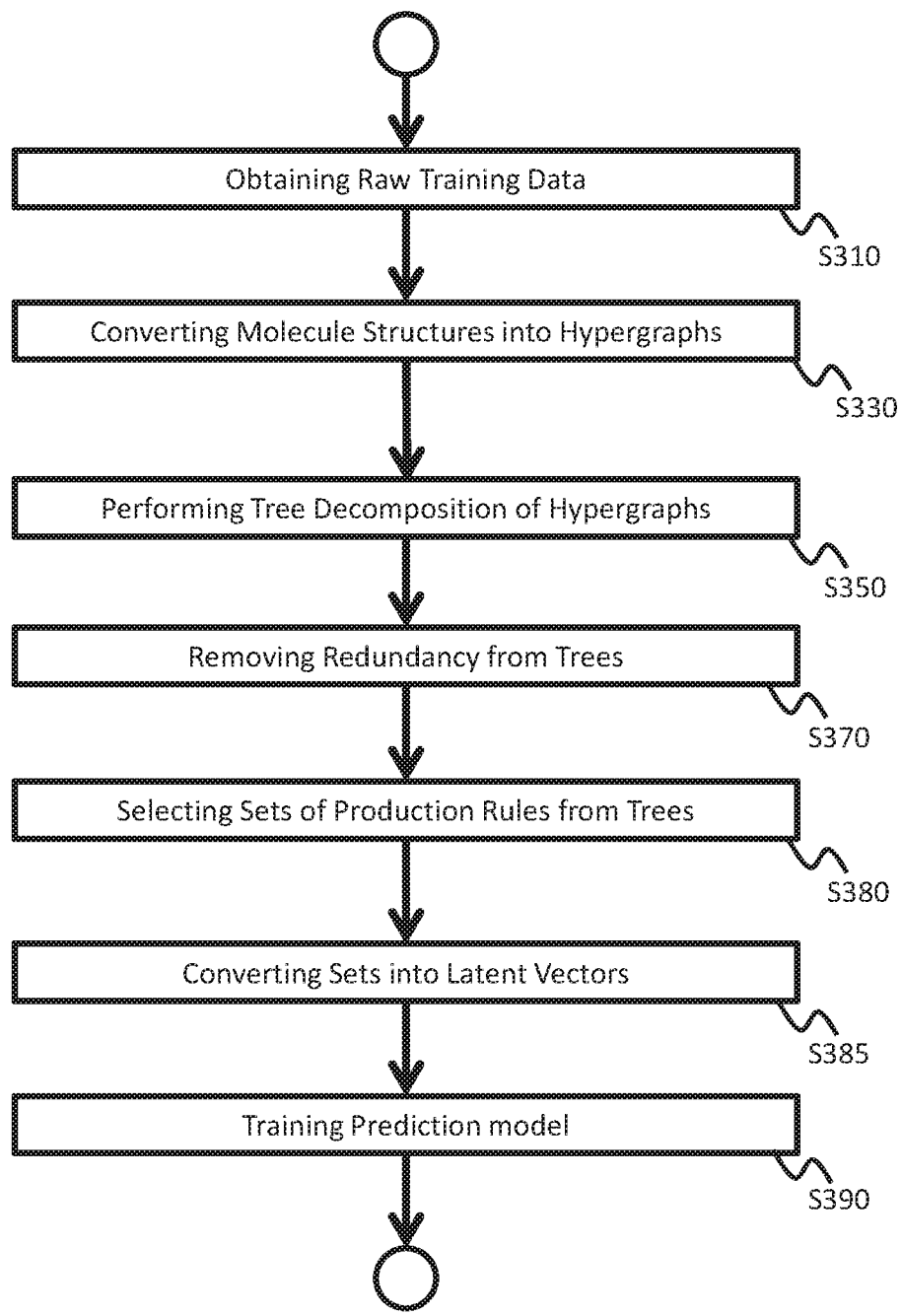
FIG. 21 shows a sub-flow of the flow in FIG. 3 according to an embodiment of the present invention.

FIG. 21 shows a sub-flow of block S300 in the flow of FIG. 3 according to an embodiment of the present invention. The apparatus may perform operations of blocks S310-S390 of FIG. 21 at the operation of block S300 of FIG. 3.

At block S310, an obtaining section, such as the obtaining section 110 (FIG. 2), may obtain raw training data. The raw training data may include a plurality of sets, each set including a molecule structure and a performance. The performance may include physical, chemical, pharmaceutical, and/or clinical characteristics of the molecule structure. In an embodiment, each set of the raw training data may include a molecule structure of a known medicine and pharmaceutical data of the known medicine.

At block S330, a hypergraph section, such as the hypergraph section 115 (FIG. 2), generates a plurality of hypergraphs from a plurality of molecule structures in the raw training data obtained at block S310. The hypergraph section generates the hypergraphs in a similar manner as explained in relation to block S130 (FIG. 4).

At block S350, a decomposition section, such as the decomposition section 120 (FIG. 2), may perform a tree decomposition of the plurality of hypergraphs generated at block S330 to obtain a plurality of trees corresponding to the plurality of hypergraphs. The decomposition section performs the tree decomposition in a similar manner as explained in relation to block S150 (FIG. 4).

At Block S370, a removing section, such as the removing section 125 (FIG. 2), may remove a redundant hypergraph node from tree nodes of the plurality of trees generated at block S350. The removing section removes the redundant hypergraph node in a similar manner as explained in relation to block S170 (FIG. 4).

At block S380, a rule processing section, such as the rule processing section 135 (FIG. 2), may select one or more production rules among the plurality of production rules that have been extracted at block S190 (FIG. 4), from each of the plurality of trees processed at block S370. The rule processing section may select production rules such that the selected production rules construct a hypergraph corresponding to each tree. The rule processing section may select production rules for each tree as each set of a plurality of sets of production rules. Each set of the plurality of production rules may include information of an order by which the production rules are applied for constructing the hypergraph.

In an embodiment, the rule processing section may first cause the extracting section to extract a set of production rules for each of the plurality of trees in a similar manner as explained in relation to block S190 (FIG. 4). Then the rule processing section may search production rules in the extracted set, among the plurality of production rules. The rule processing section may perform this search by determining whether structures (e.g., terminal symbols, non-terminal symbols, nodes, and/or connection between them) between production rules are identical or substantially identical.

At block S385, a converting section, such as the converting section 140 (FIG. 2), may convert each set of the plurality of production rules into each of a plurality of latent vectors. In an embodiment, the converting section may input each set of the plurality of production rules into the encoder of the autoencoder trained at block S250 (FIG. 20) to obtain a latent vector.

At block S390, a model training section, such as the model training section 160 (FIG. 2), may train a prediction model with a training data. In an embodiment, the model training section trains the prediction model by using training data including a plurality of sets, each set including a latent vector and a performance.

In the embodiment, the plurality of sets of a latent vector and a performance includes the plurality of latent vectors generated at block S385, and a plurality of performances of a plurality of molecule structures corresponding to the plurality of latent vectors in the raw training data. The training data includes a plurality of sets of a latent vector derived from a medicine and a performance of the medicine.

The model training section may train any known model to be the prediction model. In an embodiment, the training section trains a neural network to be the prediction model.

Figure 22:
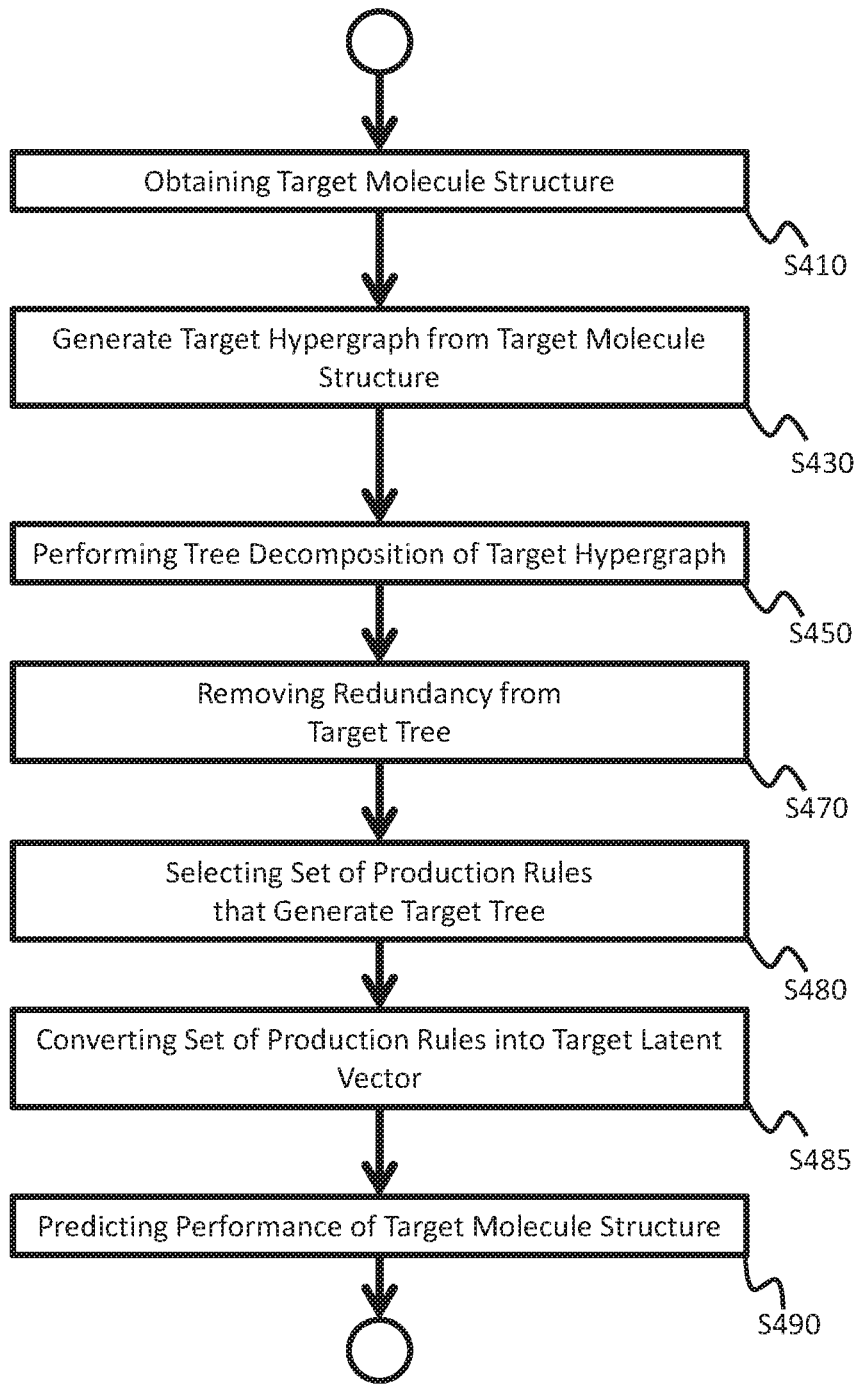
FIG. 22 shows a sub-flow of the flow in FIG. 3 according to an embodiment of the present invention.

FIG. 22 shows a sub-flow of block S400 in the flow of FIG. 3 according to an embodiment of the present invention. The apparatus may perform operations of blocks S410-S490 of FIG. 22 at the operation of block S400 of FIG. 3.

At block S410, an obtaining section, such as the obtaining section 110 (FIG. 2), may obtain a target molecule structure. The target molecule structure may be a molecule structure of which performance is to be predicted. In an embodiment, the target molecule structure may be a molecule structure of a candidate medicine.

At block S430, a hypergraph section, such as the hypergraph section 115 (FIG. 2), generates a target hypergraph from the target molecule structure. The hypergraph section may generate the target hypergraph in a similar manner as explained in relation to block S130 (FIG. 4).

At block S450, a decomposition section, such as the decomposition section 120 (FIG. 2), may perform a tree decomposition of the target hypergraph generated at block S430 to obtain a target tree corresponding to the target hypergraph. The decomposition section may perform the tree decomposition in a similar manner as explained in relation to block S150 (FIG. 4).

At block S470, a removing section, such as the removing section 125 (FIG. 2), may remove a redundant hypergraph node from tree nodes of the target tree generated at block S450. The removing section may remove the redundant hypergraph node in a similar manner as explained in relation to block S170 (FIG. 4).

At block S480, a rule processing section, such as the rule processing section 135 (FIG. 2), may select a set of production rules among the plurality of production rules that have been extracted at block S190 (FIG. 4) for the target tree processed at block S470. The rule processing section may select the set of production rules in a similar manner as explained in relation to block S380 (FIG. 21).

In an embodiment, the rule processing section may select two or more different sets of production rules for the target tree. Thereby, performance of the target molecule structure may be predicted from different aspects.

At block S485, a converting section, such as the converting section 140 (FIG. 2), may convert the set of the plurality of production rules selected at block S480 into a target latent vector. The converting section may generate the target latent vector in a similar manner as explained in relation to block S385 (FIG. 21).

At block S490, a predicting section, such as the predicting section 145 (FIG. 2), may predict a performance of the target molecule structure. In an embodiment, the predicting section may input the target latent vector obtained at block S485 into the prediction model trained at block S390 in FIG. 21 to obtain a predicted performance of the target molecule structure.

According to the operational flow in FIG. 22, the apparatus can predict the performance of a molecule by using the syntax tree of the molecule according to an HRG.

Figure 23:
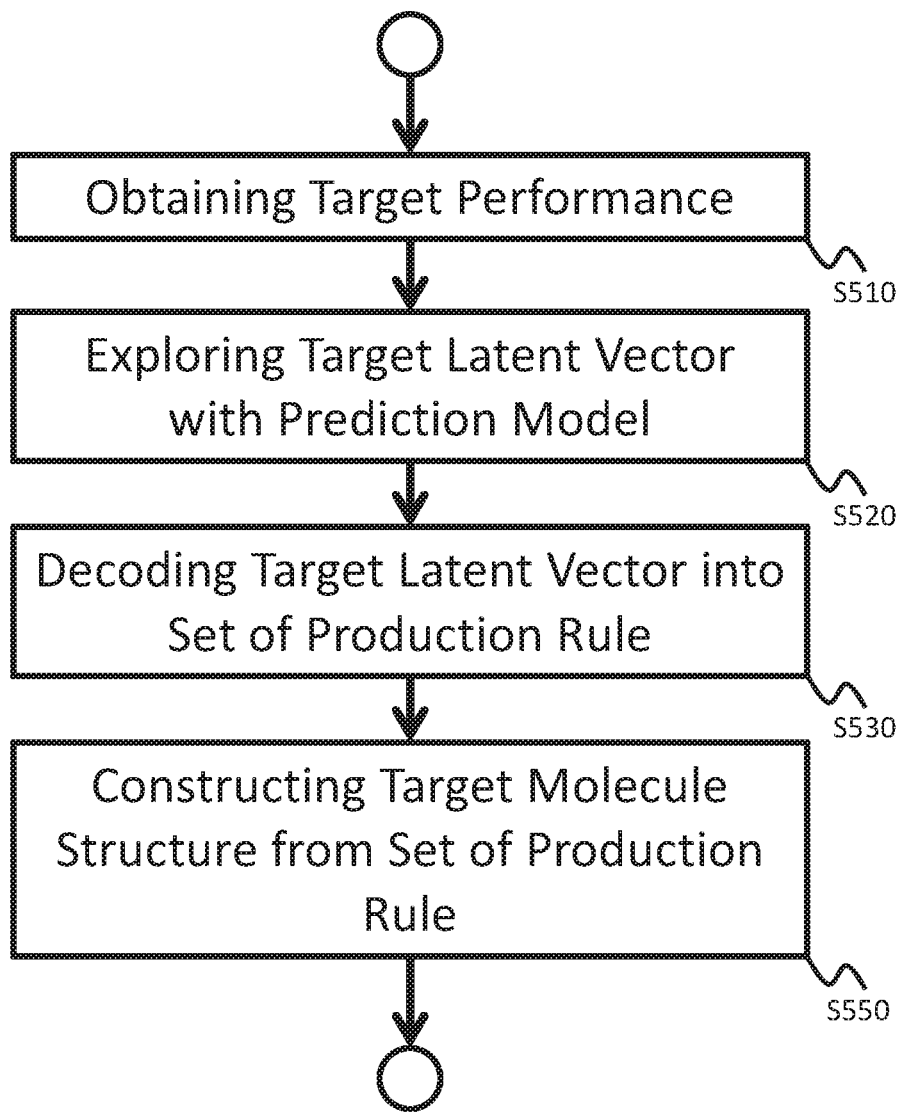
FIG. 23 shows a sub-flow of the flow in FIG. 3 according to an embodiment of the present invention.

FIG. 23 shows a sub-flow of block S400 in the flow of FIG. 3 according to another embodiment of the present invention. The apparatus may perform operations of blocks S510-S550 of FIG. 23 at the operation of block S400 of FIG. 3.

At block S510, an obtaining section, such as the obtaining section 110 (FIG. 2), may obtain a target performance. The target performance may be desired physical, chemical, pharmaceutical, and/or clinical characteristics of a molecule structure that can be predicted by the prediction model. In an embodiment, the target performance may be a desired pharmaceutical effect for a certain disease.

At block S520, an exploring section, such as the exploring section 150 (FIG. 2), may explore a target latent vector for which a target performance is obtained in response to inputting of the latent vector into the prediction model. In an embodiment, the exploring section explores the target latent vector by using a known algorithm, such as Bayesian optimization or stochastic gradient descent.

At block S530, a converting section, such as the converting section 140 (FIG. 2), may convert the target latent vector into a target set of one or more production rules. In an embodiment, the converting section may input the target latent vector into the decoder of the autoencoder trained at block S250 (FIG. 20) to obtain a target set of one or more production rules. The target set of one or more production rules may include an order in which the production rules are applied.

In an embodiment, the converting section outputs the target set as a plurality of possibilities. For example, the converting section may perform a sampling of sets of production rules by using P(r|l), where l is latent vector and r is a set of production rules. Thereby the converting section may input a latent vector $l_n$ and output K samples $r_1$, $r_2$, $r_3$, ..., $r_K$ independently sampled from $P(r|l_n)$, which are a probability distribution of a set of production rules conditioned on the latent vector $l_n$.

In an embodiment, the converting section determines the most sampled set as the target set of one or more production rules. In an embodiment, the converting section determines a predetermined number of sets having larger samples as the target sets of one or more production rules.

At block S550, a rule processing section, such as the rule processing section 135 (FIG. 2), may construct a target molecule structure from the target set of one or more production rules converted at block S530. In an embodiment, the rule processing section may first construct a target hypergraph by applying one or more production rules in the target set.

In a specific embodiment, the target set may include: (1) starting rule in FIG. 10, (2) developing rule 1 in FIG. 11, (3) developing rule 2 in FIG. 12, (4) developing rule 1, (5) developing rule 2, and (6) developing rule 2, in this order. In the embodiment, the rule processing section may construct a target hypergraph of cyclobutane described in FIG. 7 by applying (1) starting rule, (2) developing rule 1, (3) developing rule 2, (4) developing rule 1, (5) developing rule 2, and (6) developing rule 2 in this order.

Then, the rule processing section may convert the target hypergraph into a target molecule structure. In an embodiment, the rule processing section may convert hyperedges in the target hypergraph into nodes of a graph, and nodes in the target hypergraph into edges of the graph to obtain the target molecule structure. In a specific embodiment, the rule processing section may convert the hypergraph in FIG. 7 into a molecule structure of cyclobutane in FIG. 6.

According to the operational flow in FIG. 23, the apparatus can efficiently search for useful molecules. According to the embodiments above, the apparatus can output molecule structures that have correct valence, since the apparatus does not use SMILES as representative of molecules, and instead uses tree decomposition of molecule hypergraphs in which molecular connections exist as nodes.

In addition, in some embodiments above, the apparatus may remove redundancies from trees. Therefore, the apparatus may output molecule structures that have correct connections. With redundant nodes in the trees, the apparatus outputs molecule structures that have a single connection among three or more atoms.

An exemplary definition of the tree decomposition according to an embodiment of the present invention is provided by definition 2, as follows: a tree decomposition of hypergraph $H=(V_H, E_H)$ is tree $T=(V_T, E_T)$ with two labeling functions: $l_T^{(V)}:V_T \rightarrow 2^{V_H}$ and $l_T^{(E)}:V_T \rightarrow 2^{E_H}$ such that: for each $v_H \in V_H$ there exists at least one node $v_T \in V_T$ such that $v_H \in l_T^{(V)}(v_T)$, for each $e_H \in E_H$ there exists exactly one node $v_T \in V_T$ such that $e_H \subseteq l_T^{(V)}(v_T)$ and $e_H \in l_T^{(E)}(v_T)$, and for each $v_T \in V_T$ a set of nodes $\{v_E \in V_t | v_H \in l_T^{(V)}(v_T)\}$ is connected in T. In an embodiment, the decomposition section performs the tree decomposition by at least partially using definition 2.

An exemplary definition for generating the hypergraph according to an embodiment of the present invention is provided by definition 3 stating: let $L^{(E)}$ be a set of hyperedge labels, and $c^{(E)}:L^{(E)} \rightarrow \mathbb{N}$ be a cardinality constraint function; and a hyperedge-labeled hypergraph $H=(V_H, E_H, l_H^{(E)})$ is called a molecular hypergraph if: H is 2-regular, and for each $e \in E_H$, $|e|=c^{(E)}(l_H^{(E)}(e))$ holds, where $|e|$ is the cardinality of hyperedge e. In an embodiment, the hypergraph section generates a hypergraph by at least partially using definition 3.

Figure 24:
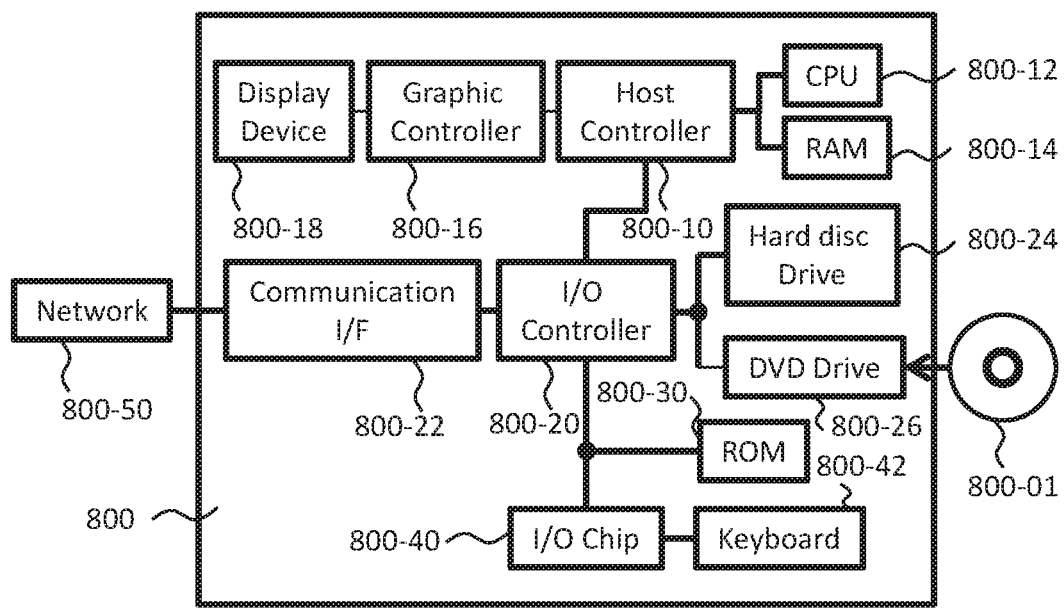
FIG. 24 shows an exemplary hardware configuration of a computer that functions as a system, according to an embodiment of the present invention.

FIG. 24 shows an exemplary hardware configuration of a computer configured for the embodiments of the present invention. A program that is installed in the computer 800 can cause the computer 800 to function as or perform operations associated with apparatuses of the embodiments of the present invention or one or more sections (including modules, components, elements, etc.) thereof, and/or cause the computer 800 to perform processes of the embodiments of the present invention or steps thereof. Such a program may be executed by the CPU 800-12 to cause the computer 800 to perform certain operations associated with some or all of the blocks of flowcharts and block diagrams described herein.

The computer 800 according to the present embodiment includes a CPU 800-12, a RAM 800-14, a graphics controller 800-16, and a display device 800-18, which are mutually connected by a host controller 800-10. The computer 800 also includes input/output units such as a communication interface 800-22, a hard disk drive 800-24, a DVD-ROM drive 800-26 and an IC card drive, which are connected to the host controller 800-10 via an input/output controller 800-20. The computer also includes legacy input/output units such as a ROM 800-30 and a keyboard 800-42, which are connected to the input/output controller 800-20 through an input/output chip 800-40.

The CPU 800-12 operates according to programs stored in the ROM 800-30 and the RAM 800-14, thereby controlling each unit. The graphics controller 800-16 obtains image data generated by the CPU 800-12 on a frame buffer or the like provided in the RAM 800-14 or in itself, and causes the image data to be displayed on the display device 800-18.

The communication interface 800-22 communicates with other electronic devices via a network 800-50. The hard disk drive 800-24 stores programs and data used by the CPU 800-12 within the computer 800. The DVD-ROM drive 800-26 reads the programs or the data from the DVD-ROM 800-01, and provides the hard disk drive 800-24 with the programs or the data via the RAM 800-14. The IC card drive reads programs and data from an IC card, and/or writes programs and data into the IC card.

The ROM 800-30 stores therein a boot program or the like executed by the computer 800 at the time of activation, and/or a program depending on the hardware of the computer 800. The input/output chip 800-40 may also connect various input/output units via a parallel port, a serial port, a keyboard port, a mouse port, and the like to the input/output controller 800-20.

A program is provided by computer readable media such as the DVD-ROM 800-01 or the IC card. The program is read from the computer readable media, installed into the hard disk drive 800-24, RAM 800-14, or ROM 800-30, which are also examples of computer readable media, and executed by the CPU 800-12. The information processing described in these programs is read into the computer 800, resulting in cooperation between a program and the above-mentioned various types of hardware resources. An apparatus or method may be constituted by realizing the operation or processing of information in accordance with the usage of the computer 800.

For example, when communication is performed between the computer 800 and an external device, the CPU 800-12 may execute a communication program loaded onto the RAM 800-14 to instruct communication processing to the communication interface 800-22, based on the processing described in the communication program. The communication interface 800-22, under control of the CPU 800-12, reads transmission data stored on a transmission buffering region provided in a recording medium such as the RAM 800-14, the hard disk drive 800-24, the DVD-ROM 800-01, or the IC card, and transmits the read transmission data to network 800-50 or writes reception data received from network 800-50 to a reception buffering region or the like provided on the recording medium.

In addition, the CPU 800-12 may cause all or a necessary portion of a file or a database to be read into the RAM 800-14, the file or the database having been stored in an external recording medium such as the hard disk drive 800-24, the DVD-ROM drive 800-26 (DVD-ROM 800-01), the IC card, etc., and perform various types of processing on the data on the RAM 800-14. The CPU 800-12 may then write back the processed data to the external recording medium.

Various types of information, such as various types of programs, data, tables, and databases, may be stored in the recording medium to undergo information processing. The CPU 800-12 may perform various types of processing on the data read from the RAM 800-14, which includes various types of operations, processing of information, condition judging, conditional branch, unconditional branch, search/ replace of information, etc., as described throughout this disclosure and designated by an instruction sequence of programs, and writes the result back to the RAM 800-14.

In addition, the CPU 800-12 may search for information in a file, a database, etc., in the recording medium. For example, when a plurality of entries, each having an attribute value of a first attribute is associated with an attribute value of a second attribute, are stored in the recording medium, the CPU 800-12 may search for an entry matching the condition whose attribute value of the first attribute is designated, from among the plurality of entries, and reads the attribute value of the second attribute stored in the entry, thereby obtaining the attribute value of the second attribute associated with the first attribute satisfying the predetermined condition.

The above-explained program or software modules may be stored in the computer readable media on or near the computer 800. In addition, a recording medium such as a hard disk or a RAM provided in a server system connected to a dedicated communication network or the Internet can be used as the computer readable media, thereby providing the program to the computer 800 via the network.

The present invention may be a system, a method, and/or a computer program product. The computer program product may include a computer readable storage medium (or media) having computer readable program instructions thereon for causing a processor to carry out aspects of the present invention. The apparatus of the embodiments of the present invention may include the computer readable medium and the processor or programmable circuitry operable to execute the instructions.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to individualize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments of the present invention have been described, the technical scope of the invention is not limited to the above described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

As made clear from the above, the embodiments of the present invention enable generation of production rules representing molecule structures.

What is claimed is:

1. A computer-implemented method, comprising:
generating a hypergraph from each of a plurality of molecule structures;
performing a tree decomposition of each hypergraph to obtain a tree corresponding to the hypergraph; and
extracting a set of production rules for producing each hypergraph, by using connections of nodes in the corresponding tree.

2. The method of claim 1, further comprising:
removing a redundant hypergraph node in a tree node in the tree decompositions before extracting the set of production rules.

3. The method of claim 1, wherein each hypergraph includes one or more hyperedges that each corresponds to an atom in a corresponding molecule structure, and one or more nodes that each corresponds to a connection between atoms in the corresponding molecule structure.

4. The method of claim 1, wherein the set of production rules include one or more starting rules that provide an initial hypergraph portion including a partial structure of the hypergraph.

5. The method of claim 4, wherein the initial hypergraph portion includes one or more non-terminal symbols.

6. The method of claim 5, wherein the set of production rules include one or more developing rules that replace a non-terminal symbol in an existing hypergraph portion with an additional hypergraph portion.

7. The method of claim 6, wherein the additional hypergraph portion includes at least one of (i) one or more non-terminal symbols and (ii) one or more terminal symbols.

8. The method of claim 1, further comprising:
training an autoencoder for a plurality of sets of production rules;
wherein the autoencoder includes an encoder that converts the set of production rules into a latent vector, and a decoder that restores the set of production rules from the latent vector; and
each set of production rules corresponds with a molecule structure among the plurality of molecule structures.

9. The method of claim 8, further comprising:
training a prediction model that predicts a performance of one of the plurality of molecule structures by inputting the latent vector corresponding to the molecule structure.

10. The method of claim 9, further comprising:
generating a target hypergraph from a target molecule structure;
performing a tree decomposition of the target hypergraph to obtain a target tree corresponding to the target hypergraph;
selecting one or more production rules among the plurality of sets of production rules for producing the target hypergraph, from connections of nodes in the target tree;
converting the one or more production rules into a target latent vector by using the encoder; and
inputting the target latent vector into the prediction model to obtain a performance of the target molecule structure.

11. The method of claim 9, further comprising:
exploring a target latent vector for which a target performance is obtained in response to inputting of the target latent vector into the prediction model;
converting the target latent vector into a target set of one or more production rules by using the decoder; and
constructing the target molecule structure from the target set of one or more production rules.

12. An apparatus comprising:
a processor or a programmable circuitry; and
one or more computer readable mediums collectively including instructions that, when executed by the processor or the programmable circuitry, cause the processor or the programmable circuitry to perform operations including:
generating a hypergraph from each of a plurality of molecule structures;
performing a tree decomposition of each hypergraph to obtain a tree corresponding to the hypergraph; and
extracting a set of production rules for producing each hypergraph, by using connections of nodes in the corresponding tree.

13. The apparatus of claim 12, wherein the operations further comprises:
removing a redundant hypergraph node in a tree node in the tree decompositions before extracting the set of production rules.

14. The apparatus of claim 12, wherein each hypergraph includes one or more hyperedges that each corresponds to an atom in a corresponding molecule structure, and one or more nodes that each corresponds to a connection between atoms in the corresponding molecule structure.

15. The apparatus of claim 12, wherein the set of production rules include one or more starting rules that provide an initial hypergraph portion including a partial structure of the hypergraph.

16. The apparatus of claim 15, wherein the initial hypergraph portion includes one or more non-terminal symbols.

17. The apparatus of claim 16, wherein the set of production rules include one or more developing rules that replace a non-terminal symbol in an existing hypergraph portion with an additional hypergraph portion.

18. The apparatus of claim 17, wherein the additional hypergraph portion includes at least one of (i) one or more non-terminal symbols and (ii) one or more terminal symbols.

19. A computer program product including one or more computer readable storage mediums collectively storing program instructions that are executable by a processor or programmable circuitry to cause the processor or programmable circuitry to perform operations comprising:
generating a hypergraph from each of a plurality of molecule structures;
performing a tree decomposition of each hypergraph to obtain a tree corresponding to the hypergraph; and
extracting a set of production rules for producing each hypergraph, by using connections of nodes in the corresponding tree.

20. The computer program product of claim 19, wherein the operations further comprises:
removing a redundant hypergraph node in a tree node in the tree decompositions before extracting the set of production rules.

21. The computer program product of claim 19, wherein each hypergraph includes one or more hyperedges that each corresponds to an atom in a corresponding molecule structure, and one or more nodes that each corresponds to a connection between atoms in the molecule structures.

22. The computer program product of claim 19, wherein the set of production rules include one or more starting rules that provide an initial hypergraph portion including a partial structure of the hypergraph.

23. The computer program product of claim 22, wherein the initial hypergraph portion includes one or more non-terminal symbols.

24. The computer program product of claim 23, wherein the set of production rules include one or more developing rules that replace a non-terminal symbol in an existing hypergraph portion with an additional hypergraph portion.

25. The computer program product of claim 24, wherein the additional hypergraph portion includes at least one of (i) one or more non-terminal symbols and (ii) one or more terminal symbols.

* * * * *